(12) United States Patent
Archibald et al.

(10) Patent No.: US 6,555,562 B1
(45) Date of Patent: Apr. 29, 2003

(54) PHENYLALANINE DERIVATIVES

(75) Inventors: Sarah Catherine Archibald; John Clifford Head, both of Maidenhead; Graham John Warrellow, Northwood; John Robert Porter, Chinnor, all of (GB)

(73) Assignee: Celltech R&D Limited, Slough (GB)

( * ) Notice: Subject to any disclaimer, the term of this patent is extended or adjusted under 35 U.S.C. 154(b) by 0 days.

(21) Appl. No.: 09/258,522

(22) Filed: Feb. 26, 1999

(30) Foreign Application Priority Data

Feb. 26, 1998 (GB) .............................................. 9804161
Dec. 3, 1998 (GB) .............................................. 9826668

(51) Int. Cl.$^7$ ...................... A61K 31/44; C07D 211/82; C07D 213/56
(52) U.S. Cl. ........................ 514/357; 546/330; 546/337
(58) Field of Search .............................. 546/329, 276.4, 546/268.4, 330, 337; 562/442; 514/357

(56) References Cited

U.S. PATENT DOCUMENTS

| | | | |
|---|---|---|---|
| 4,987,132 A | 1/1991 | Mase et al. | 514/252 |
| 5,164,372 A | 11/1992 | Matsuo et al. | 514/19 |
| 5,260,277 A | 11/1993 | McKenzie | 544/18 |
| 5,296,486 A | 3/1994 | Lazer et al. | 514/333 |
| 5,399,585 A | 3/1995 | Alig et al. | 514/438 |
| 6,093,696 A | 7/2000 | Head et al. | 514/19 |

FOREIGN PATENT DOCUMENTS

| | | |
|---|---|---|
| DE | 23 16 881 A | 10/1973 |
| DE | 28 37 264 A1 | 3/1979 |
| DE | 196 54 483 A | 1/1998 |
| EP | 0 031 104 A1 | 7/1981 |
| EP | 0 048 763 A1 | 4/1982 |
| EP | 0 144 230 A | 6/1985 |
| EP | 0 322 068 A1 | 6/1989 |
| EP | 0 394 989 A2 | 10/1990 |
| EP | 0 498 268 A2 | 8/1992 |
| EP | 0 596 406 A1 | 5/1994 |
| EP | 0 710 657 A1 | 5/1996 |
| EP | 0 710 659 A1 | 5/1996 |
| EP | 0 842 943 A2 | 5/1998 |
| EP | 0 842 945 A2 | 5/1998 |
| JP | 56 090045 | 7/1981 |
| JP | 03 135962 | 6/1991 |
| WO | WO 86/02353 | 4/1986 |
| WO | WO 93/00095 | 1/1993 |
| WO | WO 93/08174 | 4/1993 |
| WO | WO 93/09795 | 5/1993 |
| WO | WO 94/15954 | 7/1994 |
| WO | WO 94/15955 | 7/1994 |
| WO | WO 94/29285 | 12/1994 |
| WO | WO 95/13811 | 5/1995 |
| WO | WO 95/15973 | 6/1995 |
| WO | WO 95/19356 | 7/1995 |
| WO | WO 96/26190 | 8/1996 |
| WO | WO 97/12866 | 4/1997 |
| WO | WO 97/24124 | 7/1997 |
| WO | WO 97/31907 | 9/1997 |
| WO | WO 97/36859 | * 10/1997 |
| WO | WO 98/00395 | 1/1998 |
| WO | WO 98/42662 | 10/1998 |
| WO | WO 98/53814 | 12/1998 |
| WO | WO 98/53817 | 12/1998 |
| WO | WO 98/53818 | 12/1998 |
| WO | WO 98/54207 | 12/1998 |
| WO | WO 98/58902 | 12/1998 |
| WO | WO 99/06390 | 2/1999 |
| WO | WO 99/06431 | 2/1999 |
| WO | WO 99/06432 | 2/1999 |
| WO | WO 99/06433 | 2/1999 |
| WO | WO 99/06434 | 2/1999 |
| WO | WO 99/06435 | 2/1999 |
| WO | WO 99/06436 | 2/1999 |
| WO | WO 99/06437 | 2/1999 |
| WO | WO 99/10312 | 3/1999 |
| WO | WO 99/10313 | 3/1999 |
| WO | WO 99/20272 | 4/1999 |
| WO | WO 99/35163 | 7/1999 |
| WO | WO 99/37618 | 7/1999 |
| WO | WO 99/43642 | 9/1999 |
| WO | WO 99/48879 | 9/1999 |
| WO | WO 00/20396 | 4/2000 |
| WO | WO 00/31067 | 6/2000 |
| WO | WO 00/35855 | 6/2000 |
| WO | WO 00/73260 | 12/2000 |

OTHER PUBLICATIONS

Hammadi, A., et al., "Diastereoselective hydrogenation of monodehydro enkephalins controlled by chiral rhodium catalysts," *Tetrahedron: Asymmetry*, 1992, 3(10), XP002106601, 1247–1262.

Nunami, K., et al., "A novel synthesis of methyl 1,5–disubstituted imidazole–4–carboxylates using 3–bromo–2–isocyanoacrylates," *J. Org. Chem.*, 1994, 59, XP002106602, 7635–7642.

(List continued on next page.)

*Primary Examiner*—Alan L. Rotman
(74) *Attorney, Agent, or Firm*—Woodcock Washburn LLP

(57) ABSTRACT

Phenylalanine derivatives of formula (1) are described:

$$R^1(Alk^1)_r(L^1)_s\text{—}\underset{R^b}{\overset{R^a}{\text{[phenyl ring]}}}\text{—}(Alk^2)_m\text{—}C(R^2)(R)\text{—}N(R^3)COAr \quad (1)$$

wherein
  R is a carboxylic acid or a derivative thereof;
  L$^1$ is a linker atom or group;
  Ar is an optionally substituted aromatic group;
and the salts, solvates, hydrates and N-oxides thereof.

The compounds are able to inhibit the binding of alpha4 integrins to their ligands and are of use in the prophylaxis and treatment of immune or inflammatory disorders.

9 Claims, No Drawings

OTHER PUBLICATIONS

Shimohigashi, Y., et al., "Dehydro–enkephalins," *Int. J. Peptide Protein Res.,* 1983, 21, XP002106600, 202–208.

Strange, P.G., et al., "Studies of enzyme–mediated reactions. Part II. Stereochemistry of the elimination of ammonia form L–tyrosine catalysed by the enzyme from maize," *J. Chem. Soc., Perkin I,* 1972, 18, XP002106603, 2364–2372.

WPI/Derwent No. XP002106604, Japanese Patent No. JP 60 190749 (Mitsui Toatsu Chem. Inc.), Sep. 28, 1985, 1 page, Abstract only.

Rico, J.G. et al., "A highly stereoselective michael addition to an α, β–unsaturated ester as the crucial step in the synthesis of a novel β–amino acid–containing fibrinogen receptor antagonist",*J. Org. Chem,* 1993, vol. 58, pp. 7948–7951.

Zablocki, J.A. et al., "Potent in vitro and in vivo inhibitors of platelet aggregation based upon the Arg–Gly–Asp sequences of fibrinogen",*J. Med. Chem.,* 1995, vol. 38, pp. 2378–2394.

Buckle, D.R., et al., "Non Thiazolidinedione Antihyperglycaemic Agents. 1: α–Heteroatom Substituted β–Phenylpropanoic Acids," *Bioorg. Med. Chem. Lett.,* 1996, 6(17), 2121–2126.

Keenan, R.M. et al., "Discovery of Potent Nonpeptide Vitronectin Receptor (av$β_3$) Antagonists," *J. Med. Chem.,* 1997, 40(15), 2289–2292.

McDowell, R.S. et al., "From Peptide to Non–Peptide. 2. The de Novo Design of Potent, Non–Peptidal Inhibitors of Platelet Aggregation Based on a Benzodiazepinedione Scaffold," *J. Am. Chem. Soc.,* 1994, 116, 5077–5083.

Miller, W.H. et al., "Structure–Activity Relationships in 3–Oxo–1,4–Benzodiazepine–2–Acetic Acid GPIIb/IIIa Antagonists. The 2–Benzazepine Series," *Bioorg. Med. Chem. Lett.,* 1996, 6(21), 2481–2486.

Ukai, Y. et al., "A novel synthetic inhibitor of endopeptidase–24.15," *Chemical Abstracts,* 1997, 127(2), 1 page.

Venturella, V.S. et al., "Substituted 1,3–Dihydro–4H–furo [3,4–d]–1,3–benzodiazepin–3–ones: Synthesis and Scope of the Method," *J. Heterocyclic Chem.,* 1969, 6(5), 671–679.

Wojciechowska, H. et al., "Preparation of 2,4–dinitrophenyl derivatives of tyrosine," *Chemical Abstracts,* 1968, 68(25), Abstract No. 114926r, 1 page.

Clausen, K., et al., "Studies on amino acids and peptides. II. Synthesis of protected endothiodipeptides," *J. Chem. Scr.,* 1982, 20(1–2), 14–18, doc. No. 97:163474 (abstract only, 1 page).

Frank, R., et al., "Extremely mild reagent for Boc deprotection," *J. Chem. Commun. (Cambridge),* 1996, 22, 2509–2510, doc. No. 126:104395 (abstract only, 3 pages).

Kobayashi, A., et al., "Syntheses of 2–dialkylamino–4, 4–disubstituted 5 (4H)–thiazolones," *J. Yakugaku Zasshi,* 1970, 90(11), 1377–1380, doc. No. 74:31713 (abstract only, 3 pages).

Koenig, H.B., et al., ".beta.–Lactam antibiotics," *Ger. Offen.,* 41 pages, doc. No. 83:97276 (abstract only, 5 pages).

Masuda, T., *Jpn. Kodai Tokkyo Koho,* 22 pages, doc. No. 115:280022 (abstract only, 1 page).

Pfeifer, T., et al., "Specific fragmentation of thioxo peptides facilitates the assignment of the thioxylated amino acid," *J. Mass Spectrom,* 1997, 32(10), 1064–1071, doc. No. 127:331738 (abstract only 2 pages).

Sawa, N., et al., "Preparation of 4(5)–thiocarbamoylimidazole compounds," *Jpn. Kokai Tokkyo Koho,* 33 pages, doc. No. 115:183296 (abstract only, 2 pages).

Schutkowski, M., et al., "Inhibition of peptidyl–prolyl cis/trans isomerase activity by substrate analog structures: thioxo tetrapeptide–4–nitroanilides," *Biochemistry,* 1995, 34(40), 13016–13026, doc. No. 123:221511 (abstract only, 4 pages).

"Cephalosporins," *Jpn. Kokai Tokkyo Koho,* 40 pages, doc. No. 99:5433 (abstract only, 2 pages).

Bach et al., "Anomalous optical rotation and circular dichroism of N–thioacylated.alpha.–amino acids and deriva," *Acta Chem. Scand.,* 1966, 20(10), 2781–2794.

Barrett, G.C., "Circular dichroism of N–thiobenzoyl–1–α–amino acids. III. Their circular dichroism through the near–ultraviolet wavelength range," *J. Chem. Soc.,* 1967, Section C, 1–5.

*Chemical Abstracts,* "N–[4–Thiazolidinyl)carbonyl]amino acid derivatives," 1981, 95(19), Abstract No. 169173f, 1 page.

Cornforth, J.W., "Oxazoles and Oxazolones," *Chem. Penicillin,* Princeton Book Review, 1949, pp. 688, 799, and 800.

Fu, H. et al., "Preliminary study on synthesis and antitumor activity in vitro of derivatives of timonacic," *Chemicals Abstracts,* 1988, 108(17), Abstract No. 150358k, 1 page.

Harris, R.L.N. et al., *Aust. J. Chem.,* "Potential wool growth inhibitors. 2(1H)–Pyridone analogs of mimosine," 1977, 30(3), 649–655.

Hartke, K. et al., "Dithio and thiono esters. Part 61. Synthesis of α–amino dithioesters and endothiodipeptides," *J. Prakt. Chem.,* 1996, 338(3), 251–256.

Jaynes, B.H. et al., "Synthesis and In Vivo Antibacterial Activity of Hygromycin a Analogs Modified at the $C_4'$ Aryl Position," *Bioorg. Med. Chem. Letts.,* 1993, 3(8), 1531–1536.

Jepson, J.B. et al., "Reactions of α–Thioacylamino–acids. Their conversion into Thiazolones and Derivatives Thereof," *J. Chem. Soc.,* 1955, 1791–1797.

Masahiko, N., Japanese Patent No. 57–080370 published May 19, 1982, "Alpha–Methylcinnamic Acid Derivative, its Preparation and Antilipemic Agent Containing The Same," *Patent Abstracts of Japan,* 1982, 1 page.

Noike, Y., "Synthesis of Quinolizine Derivatives. VI. Synthesis of 3–Aminoquinolizines. (1). Synthesis of dl–3–Amino–, dl–3–epi–Amino–, and dl–3–epi–Dimethylaminoquinolizidines," *Yakugaku Zasshi,* 1959, 79(12), 1514–1518 (English summary included).

Ohki, S. et al., "Synthesis of quinolizine derivatives. V. Studies on Diastereoisomer of Ethyl 3–Quinolizidinecarboxylate," *Chem. Pharm. Bull.,* 1959, 7(6), 708–712.

Schultz, Von O.–E. et al., "Analogos of nuleic acid based as antimetabolites," *Arzneimittel Forschung. Drug Res.,* 1967, 17(8), 1060–1064 (English summary included).

Tsunematsu, H. et al., "Hydrolysis of phenylthiazolones of p–guanidinophenylalanine and arginine by trypsin and related enzymes," *J. Biochem.,* 1983, 94(4), 1119–1125.

Whitlock, B.J. et al., "Structure and synthesis of lathyrine," *J. Org. Chem.,* 1965, 30, 115–118.

Abraham, W.M. et al., "$α_4$–Integrins Mediate Antigen–Induced Late Bronchial Responses and Prolonged Airway Hyperresponsiveness in Sheep", *J. Clin. Invest.,* 1994, 93, 776–787.

Berlin, C. et al., "α4β7 Integrin Mediates Lymphocyte Binding to the Mucosal Vascular Addressin MAdCAM–1", *Cell,* 1993, 74, 185–195.

Binns, R.M. et al., "The Role of E–Selectin in Lymphocyte and Polymorphonuclear Cell Recruitment into Cutaneous Delayed Hypersensitivity Reactions in Sensitized Pigs", *J. Immunol.*, 1996, 157, 4094–4099.

Briskin, M.J. et al., "Structural Requirements for Mucosal Vascular Addressin Binding to Its Lymphocyte Receptor $\alpha_4\beta_7$", *J. Immunol.*, 1996, 156, 719–726.

Cardarelli, P.M. et al., "Cycle RGD Peptide Inhibits α4β7 Interaction with Connecting Segment 1 and Vascular Cell Adhesion Molecule", *J. Biol. Chem.*, 1994, 269(28), 18668–18673.

Ferguson, T.A. et al., "Two integrin–binding peptides abrogate T cell–mediated immune responses in vivo", *Proc. Natl. Acad. Sci. USA*, 1991, 88, 8072–8076.

Holzmann, B. et al., "Peyer's patch–specific lymphocyte homing receptors consist of a VLA–4–like α chain associated with either of two integrin β chains, one of which is novel", *EMBO J.*, 1989, 8(6), 1735–1741.

Humphries, M.J. et al., "Mechanisms of VCAM–1 and fibronectin binding to integrin $\alpha_4\beta_1$: implications for integrin function and rational drug design", *Ciba Foundation Symposium*, 1995, 189, 177–194.

Issekutz, T.B., "Inhibition of Lymphocyte Endothelial Adhesion and In Vivo Lymphocyte Migration to Cutaneous Inflammation by TA–3, a New Monoclonal Antibody to Rat LFA–1", *J. Immunol.*, 1992, 149(10), 3394–3402.

Li, Z. et al., "Effect of an anti–Mo1 MAb on ozone–induced airway inflammation and airway hyperresponsiveness in dogs", *Am. J. Physiol.*, 1992, 263(6 Pt 1), L723–726.

Marlin, S.D. et al., "LFA–1 Immunodeficiency Disease", *J. Exp. Med.*, 1986, 164, 855–867.

Osborn, L. et al., "Direct Expression Cloning of Vascular Cell Adhesion Molecule 1, a Cytokine–Induced Endothelial Protein that Binds to Lymphocytes", *Cell*, 1989, 59, 1203–1211.

Podolsky, D.K. et al., "Attenuation of Colitis in the Cotton–top Tamarin by Anti–α4 integrin Monoclonal Antibody", *J. Clin. Invest.*, 1993, 92, 372–380.

Shroff, H.N. et al., "Small Peptide Inhibitors of $\alpha_4\beta_7$ Mediated MAdCAM–1 Adhesion to Lymphocytes", *Barge. Med. Chem. Letts.*, 1996, 6(21), 2495–2500.

Sonnenberg, A., "Integrins and Their Ligands", *Curr. Topics Microbiol. Immunol.*, 1993, 184, 7–35.

Springer, T.A., "Adhesion receptors of the immune system", *Nature*, 1990, 346, 425–434.

Springer, T.A., "Traffic Signals for Lymphocyte Recirculation and Leukocyte Emigration: The Multistep Paradigm", *Cell*, 1994, 76, 301–314.

Vanderslice, P. et al., "A Cyclic Hexapeptide is a Potent Antagonist of α4 Integrins", *J. Immunol.*, 1997, 158, 1710–1718.

Yang, X., "A predominant role of integrin α4 in the spontaneous development of autoimmune diabetes in nonobese diabetic mice", *Proc. Natl. Acad. Sci. USA*, 1994, 91, 12604–12608.

Yednock, T.A., "Prevention of experimental autoimmune encephalomyelitis by antibodies against α4β1 integrin", *Nature*, 1992, 356, 63–66.

WPI / Derwent No. XP–002076854, Japanese Patent No. JP 04 193 895 A (Ajinomoto, K.K.), Jul. 13, 1992, DW9234, 1 Page, Abstract Only.

WPI / Derwent No. XP–002076855, Japanese Patent No. JP 56 049 373 A (Dainippon Pharm Co Ltd), May 2, 1981, DW8125, 1 Page, Abstract Only.

Yanagisawa, H. et al., WO 97/37970, "Preparation of phenylalkylcarboxylic acid derivatives lowering blood sugar level," *Chemical Abstracts*, 1997, Abstract 127:307307, 4 pages.

Abraham, W.M. et al., "$\beta_4$–Integrins Mediate Antigen–Induced Late Bronchial Responses and Prolonged Airway Hyperresponsiveness in Sheep", *J. Clin. Invest.*, 1994, 93, 776–787.

Berlin, C. et al., "α4β7 Integrin Mediated Lymphocyte Binding to the Mucosal Vascular Addressin MAdCAM–1", *Cell*, 1993, 74, 185–195.

Binns, R.M. et al., "The Role of E–Selection in Lymphocyte and Polymorphonuclear Cell Recruitment into Cutaneous Delayed Hypersensitivity Reactions in Sensitized Pigs", *J. Immunol.*, 1996, 157, 4094–4099.

Briskin, M.J. et al., "Structural Requirements for Mucosal Vascular Addressin Binding to Its Lymphocyte Receptor $\alpha_4\beta_7$", J. Immunol., 1996,156, 719–726.

Cardarelli, P.M. et al., "Cyclic RGD Peptide Inhibits α4β7 Interaction with Connecting Segment 1 and Vascular Cell Adhesion Molecule", J. Biol. Chem., 1994, 269(17), 18668–18673.

Ferguson, T.A. et al., "Two integrin–binding peptides abrogate T cell–mediated immune responses in vivo", *Proc. Natl. Acad. Sci. USA*, 1991, 88, 8072–8076.

Holzmann, B. et al., "Peyer's patch specific lymphocyte homing receptors consist of VLA–4–like αchain associated with either of two integrin β chains, one of which is novel", EMBO J., 1989, 8(6), 1735–1741.

Humphries, M.J. et al., "Mechanisms of VCAM–1 and fibronectin binding to integrin $\alpha_4\beta_1$ : implications for integrin function and rational drug design", *Ciba Foundation Symposium*, 1995, 189, 177–194.

Issekutz, T. B., "Inhibition of Lympocyte Endothelial Adhesion and In Vivo Lymphocyte Migration to Cutaneous Inflammation by TA–3, a New Monoclonal Antibody to Rat LFA–1", *J. Immunol.*, 1992, 149(10), 3394–3402.

Li, Z., et al., "Effect of an anti–Mol MAb on ozone–induced airway inflammation and airway hyperresponsive in dogs", *Am. J. Physiol.*, 1992, 263(6 Pt 1), L723–726.

Marlin, S.D. et al., "LFA–1 Immunodeficiency Disease", *J. Exp. Med.*, 1986, 164, 855–867.

Osborn, L. et al., "Direct Expression Cloning of Vascular Cell Adhesion Molecule 1 Cytokine–Induced Endothelial Protein that Binds to Lymphocytes", *Cell*, 1989, 59, 1203–1211.

Podolsky, D.K. et al., "Attenuation of Colitis in the Cotton–top Tamarin by Anti–β4 integrin Monoclonal Antibody", *J. Clin. Invest.*, 1993, 92, 372–380.

Shroff, H.N. et al., "Small Peptide Inhibitors of $\alpha_4\beta_7$ Mediated MAdCAM–1 Adhesion to Lymphocytes", *Barge. Med. Chem. Letts.*, 1996, 6(21), 2495–2500.

Sonnenberg, A., "Integrins and Their Ligands", *Curr. Topics Microbiol. Immunol.*, 1993, 184, 7–35.

Springer, T.A., "Adhesion receptors of the immune system", *Nature*, 1990, 346, 425–434.

Springer, T.A., "Traffic Signals for Lymphocyte Recirculation and Leukocyte Emigration: The Multistep Paradigm", *Cell*, 1994, 76, 301–314.

Vanderslice, P. et al., "A Cyclic Hexapeptide is a Potent Antagonist of α4 Integrins", *J. Immunol.*, 1997, 158, 1710–1718.

Yang, X., "A predominant role of integrin α4 in the spontaneous development of autoimmune diabetes in nonobese diabetic mice", *Proc. Natl. Acad. Sci. USA*, 1994, 91, 12604–12608.

Yednock, T.A., "Prevention of experimental autoimmune encephalomyelitis by antibodies against α4α1 integrin", *Nature*, 1992, 356, 63–66.

WPI/Derwent No. XP–002076854, Japanese Patent No. JP 04 193 895 A (Ajinomoto, K.K.) Jul. 13, 1992, DW9234, 1 page, Abstract Only.

WPI/Derwent No. XP–002076855, Japanese Patent No. JP 56 049 373 A (Dainippon Pharm Co Ltd), May 2, 1981, DW 8125, 1 page, Abstract Only.

* cited by examiner

PHENYLALANINE DERIVATIVES

This invention relates to a series of phenylalanine derivatives, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T.A. Nature, 346, 425, (1990); Springer, T. A. Cell 76, 301, (1994)]. Many of these interactions are mediated by specific cell surface molecules collectively referred to as cell adhesion molecules.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 14 different integrin alpha chains and 8 different integrin beta chains have been identified [Sonnenberg, A. Current Topics in Microbiology and Immunology, 184, 7, (1993)]. The members of the family are typically named according to their heterodimer composition although trivial nomenclature is widespread in this field. Thus the integrin termed $\alpha 4\beta 1$ consists of the integrin alpha 4 chain associated with the integrin beta 1 chain, but is also widely referred to as Very Late Antigen 4 or VLA4. Not all of the potential pairings of integrin alpha and beta chains have yet been observed in nature and the integrin family has been subdivided into a number of subgroups based on the pairings that have been recognised [Sonnenberg, A. ibid].

The importance of cell adhesion molecules in human leukocyte function has been further highlighted by a genetic deficiency disease called Leukocyte Adhesion Deficiency (LAD) in which one of the families of leukocyte integrins is not expressed [Marlin, S. D. et al J. Exp. Med. 164, 855 (1986)]. Patients with this disease have a reduced ability to recruit leukocytes to inflammatory sites and suffer recurrent infections which in extreme cases may be fatal.

The potential to modify adhesion molecule function in such a way as to beneficially modulate immune and inflammatory responses has been extensively investigated in animal models using specific monoclonal antibodies that block various functions of these molecules [e.g. Issekutz, T. B. J. Immunol. 3394, (1992); Li, Z. et al Am. J. Physiol. 263, L723, (1992); Binns, R. M. et al J. Immunol. 157, 4094, (1996)]. A number of monoclonal antibodies which block adhesion molecule function are currently being investigated for their therapeutic potential in human disease.

One particular integrin subgroup of interest involves the $\alpha 4$ chain which can pair with two different beta chains $\beta 1$ and $\beta 7$ [Sonnenberg, A. ibid]. The $\alpha_4\beta_1$ pairing occurs on many circulating leukocytes (for example lymphocytes, monocytes and eosinophils) although it is absent or only present at low levels on circulating neutrophils. $\alpha_4\beta_1$ binds to an adhesion molecule (Vascular Cell Adhesion Molecule-1 also known as VCAM-1) frequently up-regulated on endothelial cells at sites of inflammation [Osborne, L. Cell, 62, 3, (1990)]. The molecule has also been shown to bind to at least three sites in the matrix molecule fibronectin [Humphries, M. J. et al. Ciba Foundation Symposium, 189, 177, (1995)]. Based on data obtained with monoclonal antibodies in animal models it is believed that the interaction between $\alpha_4\beta 1$ and ligands on other cells and the extracellular matrix plays an important role in leukocyte migration and activation [Yednock, T. A. et al, Nature, 356, 63, (1992); Podolsky, D. K. et al. J. Clin. Invest. 92, 373, (1993); Abraham, W. M. et al. J. Clin. Invest. 93, 776, (1994)].

The integrin generated by the pairing of $\alpha 4$ and $\beta 7$ has been termed LPAM-1 [Holzmann, B and Weissman, I. EMBO J. 8, 1735, (1989)] and like $\alpha_4\beta_1$, binds to VCAM-1 and fibronectin. In addition, $\alpha_4\beta 7$ binds to an adhesion molecule believed to be involved in the homing of leukocytes to mucosal tissue termed MAdCAM-1 [Berlin, C. et al, Cell: 74, 185, (1993)]. The interaction between $\alpha_4\beta_7$ and MAdCAM-1 may also be important at sites of inflammation outside of mucosal tissue [Yang, X-D. et al, PNAS, 91, 12604 (1994)].

Regions of the peptide sequence recognised by $\alpha_4\beta_1$ and $\alpha_4\beta_7$ when they bind to their ligands have been identified. $\alpha_4\beta_1$ seems to recognise LDV, IDA or REDV peptide sequences in fibronectin and a QIDSP sequence in VCAM-1 [Humphries, M. J. et al, ibid] whilst $\alpha_4\beta_7$ recognises a LDT sequence in MAdCAM-1 [Briskin, M. J. et al, J. Immunol. 156, 719, (1996)]. There have been several reports of inhibitors of these interactions being designed from modifications of these short peptide sequences [Cardarelli, P. M. et al J. Biol. Chem. 269, 18668, (1994); Shroff, H. N. Bioorganic. Med. Chem. Lett. 6, 2495, (1996); Vanderslice, P. J. Immunol. 158, 1710, (1997)]. It has also been reported that a short peptide sequence derived from the $\alpha_4\beta_1$ binding site in fibronectin can inhibit a contact hypersensitivity reaction in a trinitrochlorobenzene sensitised mouse [Ferguson, T. A. et al, PNAS 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family it is very important to be able to identify selective inhibitors of the alpha 4 subgroup.

We have now found a group of compounds which are potent and selective inhibitors of $\alpha 4$ integrins. Members of the group are able to inhibit $\alpha 4$ integrins such as $\alpha_4\beta_1$ and/or $\alpha_4\beta_7$ at concentrations at which they generally have no or minimal inhibitory action on a integrins of other subgroups. The compounds are thus of use in medicine, for example in the prophylaxis and treatment of immune or inflammatory disorders as described hereinafter.

Thus according to one aspect of the invention we provide a compound of formula (1)

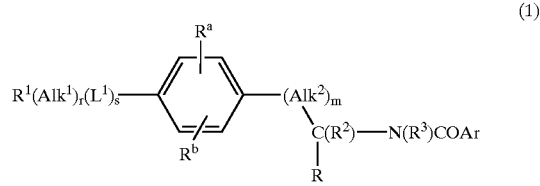

wherein

R is a carboxylic acid or a derivative thereof;

$R^1$ is a hydrogen atom or a hydroxyl, straight or branched alkoxy or optionally substituted cycloaliphatic, polycycloaliphatic, hetero-cycloaliphatic, polyheterocycloaliphatic, aromatic or heteroaromatic group;

$Alk^1$ is an optionally substituted aliphatic or heteroaliphatic chain;

$L^1$ is a linker atom or group;

r and s, which may be the same or different, is each zero or an integer 1 provided that when r is zero $R^1$ is an optionally substituted cycloaliphatic, polycycloaliphatic, polyheterocycloaliphatic, aromatic or heteroaromatic group;

$R^a$ and $R^b$, which may be the same or different is each an atom or group —$L^2(CH_2)_pL^3(R^c)_q$ in which $L^2$ and $L^3$ is each a covalent bond or a linker atom or group, p is zero or the integer 1, q is an integer 1, 2 or 3 and $R^c$ is a hydrogen or halogen atom or a group selected from straight or branched alkyl, —$OR^d$ [where $R^d$ is a hydrogen atom or an optionally substituted straight or branched alkyl group], —$SR^d$, —$NR^dR^e$, [where $R^e$ is as just defined for $R^d$ and may be the same or different], —$NO_2$, —CN, —$CO_2R_d$, —$SO_3H$, —$SO_2R^d$, —$OCO_2R^d$, —$CONR^dR^e$, —$OCONR^dR^e$, —$CSNR^dR^e$, —$COR^d$, —$N(R^d)COR^e$, $N(R^d)CSR^e$, —$SO_2N(R^d)(R^e)$, —$N(R^d)SO_2R^e$, —$N(R^d)CONR^eR^f$ [where $R^f$ is a hydrogen atom or an optionally substituted straight or branched alkyl group], —$N(R^d)CSNR^eR^f$ or —$N(R^d)SO_2NR^eR^f$;

$Alk^2$ is a straight or branched alkylene chain;

m is zero or an integer 1;

$R^2$ is a hydrogen atom or a methyl group;

$R^3$ is a hydrogen atom or a straight or branched alkyl group;

Ar is an optionally substituted aromatic group;

and the salts, solvates, hydrates and N-oxides thereof, for use in modulating cell adhesion.

The compounds of formula (1) are potent and selective inhibitors of α4 integrins. The ability of the compounds to act in this way may be simply determined by employing tests such as those described in the Examples hereinafter. In particular compounds of the invention are advantageously selective $α_4β_1$ inhibitors The compounds of formula (1) are thus of use in modulating cell adhesion and in particular are of use in the prophylaxis and treatment of diseases or disorders involving inflammation in which the extravasation of leukocytes plays a role. The invention extends to such a use and to the use of compounds of formula (1) for the manufacture of a medicament for treating such diseases or disorders. Diseases or disorders of this type include inflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds of formula (1) may be administered as pharmaceutical compositions, and according to a further aspect of the invention we provide a pharmaceutical composition which comprises a compound of formula (1) together with one or more pharmaceutically acceptable carriers, excipients or diluents, for use in modulating cell adhesion, particularly in the prophylaxis and treatment of diseases or disorders involving inflammation as just described.

Pharmaceutical compositions for use according to the invention may take a form suitable for oral, buccal, parenteral, nasal, topical or rectal administration, or a form suitable for administration by inhalation or insufflation and the invention extends to the use of a compound of formula (1) in the manufacture of such formulations.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of formula (1) required for the prophylaxis or treatment of a particular condition will vary depending on the compound chosen, and the condition of the patient to be treated. In general, however, effective daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

Particular compounds of formula (1) form a further feature of the invention and in a further aspect we therefore provide a compound of formula (1a):

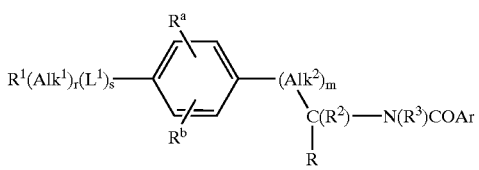

(1a)

wherein
R is a carboxylic acid or a derivative thereof;
R$^1$ is an optionally substituted cycloaliphatic, polycycloaliphatic, heterocycloaliphatic. polyheterocyclialiphatic, aromatic or heteroaromatic group;
Alk$^1$ is an optionally substituted aliphatic or heteroaliphatic chain;
L$^1$ is a linker atom or group;
r and s, which may be the same or different, is each zero or an integer 1; R$^a$ and R$^b$, which may be the same or different is each an atom or group —L$^2$(CH$_2$)$_p$L$^3$(R$^c$)$_q$ in which L$^2$ and L$^3$ is each a covalent bond or a linker atom or group, p is zero or the integer 1, q is an integer 1, 2 or 3 and R$^c$ is a hydrogen or halogen atom or a group selected from straight or branched alkyl, OR$^d$ [where R$^d$ is a hydrogen atom or an optionally substituted straight or branched alkyl group], —SR$^d$, —NR$^d$R$^e$, [where R$^e$is as just defined for R$^d$ and may be the same or different], —NO$_2$,—CN, —CO$_2$R$^d$, —SO$_3$H, —SO$_2$R$^d$, —OCO$_2$R$^d$, —CONR$^d$R$^e$, —OCONR$^d$R$^e$, —CSNR$^d$R$^e$, —COR$^d$, —N(R$^d$)COR$^e$, N(R$^d$)CSR$^e$, —SO$_2$N(R$^d$)(R$^e$), —N(R$^d$)SO$_2$R$^e$, —N(R$^d$)CONR$^e$R$^f$ [where R$^f$ is a hydrogen atom or an optionally substituted straight or branched alkyl group], —N(R$^d$)CSNR$^e$R$^f$ or —N(R$^d$)SO$_2$NR$^e$R$^f$;
Alk$^2$ is a straight or branched alkylene chain;
m is zero or an integer 1;
R$^2$ is a hydrogen atom or a methyl group;
R$^3$ is a hydrogen atom or a straight or branched alkyl group;
Ar is an optionally substituted aromatic group;
and the salts, solvates, hydrates and N-oxides thereof.

It will be appreciated that compounds of formulae (1) and (1a) may have one or more chiral centres. Where one or more chiral centres is present, enantiomers or diastereomers may exist, and the invention is to be understood to extend to all such enantiomers, diastereomers and mixtures thereof, including racemates. Formulae (1) and (1a) and the formulae hereinafter are intended to represent all individual isomers and mixtures thereof, unless stated or shown otherwise.

In the compounds of formulae (1) and (1a), derivatives of the carboxylic acid group R include carboxylic acid esters and amides. Particular esters and amides include —CO$_2$Alk$^4$ and —CON(R$^4$)$_2$ groups as described herein.

When in the compounds of formulae (1) and (1a) L$^1$ is present as a linker atom or group it may be any divalent linking atom or group. Particular examples include —O— or —S— atoms or —C(O)—, —C(O)O—, —C(S)—, —S(O)—, —S(O)$_2$—, —N(R$^4$)— [where R$^4$ is a hydrogen atom or a straight or branched alkyl group], —CON(R$^4$)—, —OC(O)N(R$^4$)—, —CSN(R$^4$)—, —N(R$^4$)CO—, —N(R$^4$)C(O)O—, —N(R$^4$)CS—, —S(O)N(R$^4$)—, —S(O)$_2$N(R$^4$)—, —N(R$^4$)S(O)—, —N(R$^4$)S(O)$_2$—, —N(R$^4$)CON(R$^4$)—, —N(R$^4$)CSN(R$^4$)—, —N(R$^4$)SON(R$^4$)— or —N(R$^4$)SO$_2$N(R$^4$)— groups. Where the linker group contains two R$^4$ substituents, these may be the same or different.

Alk$^2$ in the compounds of formulae (1) and (1a) may be for example a straight or branched C$_{1-3}$alkylene chain. Particular examples include —CH$_2$—, —CH(CH$_3$)—, —C(CH$_3$)$_2$— and —(CH$_2$)$_2$—.

When R$^3$ and/or R$^4$ in the compounds of formula (1) is a straight or branched alkyl group it may be a straight or branched C$_{1-6}$ alkyl group, e.g. a C$_{1-3}$ alkyl group such as a methyl or ethyl group.

When Alk$^1$ in compounds of formula (1) is an optionally substituted aliphatic chain it may be an optionally substituted C$_{1-10}$ aliphatic chain. Particular examples include optionally substituted straight or branched C$_{1-6}$ alkylene, C$_{2-6}$ alkenylene, or C$_{2-6}$ alkynylene chains.

Heteroaliphatic chains represented by Alk$^1$ include the aliphatic chains just described but with each chain additionally containing one, two, three or four heteroatoms or heteroatom-containing groups. Particular heteroatoms or groups include atoms or groups L$^4$ where L$^4$ is as defined above for L$^1$ when L$^1$ is a linker atom or group. Each L$^4$ atom or group may interrupt the aliphatic chain, or may be positioned at its terminal carbon atom to connect the chain to the atom or group R$^1$.

Particular examples of aliphatic chains represented by Alk$^1$ include optionally substituted —CH$_2$—, —CH$_2$CH$_2$—, —CH(CH$_3$)—, —C(CH$_3$)$_2$—, —(CH$_2$)$_2$CH$_2$—, —CH(CH$_3$)CH$_2$—, —(CH$_2$)$_3$CH$_2$—, —CH(CH$_3$)CH$_2$CH$_2$—, —CH$_2$CH(CH$_3$)CH$_2$—, —C(CH$_3$)$_2$CH$_2$—, —(CH$_2$)$_4$CH$_2$—, —(CH$_2$)$_5$CH$_2$—, —CHCH—, —CHCHCH$_2$—, —CH$_2$CHCH—, —CHCHCH$_2$CH$_2$—, —CH$_2$CHCHCH$_2$—, —(CH$_2$)$_2$CHCH—, —CC—, —CCCH$_2$—, —CH$_2$CC—, —CCCH$_2$CH$_2$—, —CH$_2$CCCH$_2$—, or —(CH$_2$)$_2$CC— chains. Where appropriate each of said chains may be optionally interrupted by one or two atoms and/or groups L$^4$ to form an optionally substituted heteroaliphatic chain. Particular examples include optionally substituted —L$^4$CH$_2$—, —CH$_2$L$^4$CH$_2$—, —L$^4$(CH$_2$)$_2$—, —CH$_2$L$^4$(CH$_2$)$_2$—, —(CH$_2$)$_2$L$^4$CH$_2$—, —L$^4$(CH$_2$)$_3$— and —(CH$_2$)$_2$L$^4$(CH$_2$)$_2$— chains.

The optional substituents which may be present on aliphatic or heteroaliphatic chains represented by Alk$^1$ include one, two, three or more substituents selected from halogen atoms, e.g. fluorine, chlorine, bromine or iodine atoms, or hydroxyl, C$_{1-6}$alkoxy, e.g. methoxy or ethoxy, thiol, C$_{1-6}$alkylthio e.g. methylthio or ethylthio, amino or substituted amino groups. Substituted amino groups include —NHR$^4$ and —N(R$^4$)$_2$ groups where R$^4$ is a straight or branched alkyl group as defined above. Where two R$^4$ groups are present these may be the same or different. Particular examples of substituted chains represented by Alk$^1$ include those specific chains just described substituted by one, two, or three halogen atoms such as fluorine atoms, for example chains of the type —CH(CF$_3$)—, —C(CF$_3$)$_2$— CH$_2$CH(CF$_3$)—, —CH$_2$C(CF$_3$)$_2$—, —CH(CF$_3$)— and —C(CF$_3$)$_2$CH$_2$.

Alkoxy groups represented by R$^1$ in compounds of formula (1) include straight of branched C$_{1-6}$alkoxy groups such as methoxy and ethoxy groups.

When R$^1$ is present in compounds of formulae (1) and (1a) as an optionally substituted cycloaliphatic group it may be an optionally substituted C$_{3-10}$ cycloaliphatic group. Particular examples include optionally substituted C$_{3-10}$ cycloalkyl, e.g. C$_{3-7}$cycloalkyl, C$_{3-10}$ cycloalkenyl e.g. C$_{3-7}$cycloalkenyl or C$_{3-10}$cycloalkynyl e.g. C$_{3-7}$cycloalkynyl groups.

Optionally substituted heterocycloaliphatic groups represented by R$^1$ include the optionally substituted cycloaliphatic groups just described for R$^1$ but with each group additionally containing one, two, three or four heteroatoms or heteroatom-containing groups $L^2$ as just defined.

Optionally substituted polycycloaliphatic groups represented by $R^1$ include optionally substituted $C_{7-10}$ bi- or tricycloalkyl or $C_{7-10}$ bi- or tricycloalkenyl groups. Optionally substituted polyheterocycloaliphatic groups represented by $R^1$ include the optionally substituted polycycloalkyl groups just described, but with each group additionally containing one, two, three or four $L^2$ atoms or groups.

Particular examples of $R^1$ cycloaliphatic, polycycloaliphatic, heterocyclo-aliphatic and polyheterocycloaliphatic groups include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, adamantyl, norbornyl, norbornenyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, thiazolinyl, thiazolidinyl, pyranyl, e.g. 2- or 4-pyranyl, piperidinyl, piperidinone, 1,4-dioxanyl, morpholinyl, morpholinone, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4- oxazinyl, 1,2,5-oxathiazinyl, isoxazinyl, e.g. o- or p-isoxazinyl, oxathiazinyl, e.g. 1,2,5 or 1,2,6-oxathiazinyl, or oxadiazinyl e.g. 1,3,5-oxodiazinyl groups.

The optional substituents which may be present on the $R^1$ cycloaliphatic, polycycloaliphatic, heterocycloaliphatic or polyheterocycloaliphatic groups include one, two, three or more substituents represented by $R^5$ in which $R^5$ is selected from halogen atoms, e.g. fluorine, chlorine, bromine or iodine atoms, or $C_{1-6}$alkyl, e.g. methyl or ethyl, halo$C_{1-6}$alkyl, e.g. halomethyl or haloethyl such as difluoromethyl or trifluoromethyl, hydroxyl, $C_{1-6}$alkoxy, e.g. methoxy or ethoxy, halo$C_{1-6}$alkoxy, e.g. halomethoxy or haloethoxy such as difluoromethoxy or trifluoromethoxy, thiol, $C_{1-6}$alkylthio e.g. methylthio or ethylthio, —N($R^4$)$_2$, —CN, —CO$_2R^4$, —NO$_2$, —CON($R^4$)$_2$, —CSN($R^4$)$_2$, —COR$^4$, —CSN($R^4$)$_2$, —N($R^4$)COR$^4$, —N($R^4$)CSR$^4$, —SO$_2$N($R^4$)$_2$, —N($R^4$)SO$_2R^4$, —N($R^4$)CON($R^4$)$_2$, —N($R^4$)CSN($R^4$) and —N($R^4$)SO$_2$N($R^4$)$_2$, groups. In these substituents the group $R^4$ when present is a hydrogen atom or a straight or branched alkyl group as defined above. Where more than one $R^4$ group is present in a substituent each group may be the same or different. The substituent may be present on any available carbon atom or where appropriate any nitrogen atom, in the $R^1$ group.

In the compounds of formulae (1) and (1a), optionally substituted aromatic groups represented by the group $R^1$ include for example monocyclic or bicyclic fused ring $C_{6-12}$ aromatic groups, such as phenyl, 1- or 2- naphthyl, 1- or 2-tetrahydronaphthyl, indanyl or indenyl groups, optionally substituted by one, two, three or more $L^2(CH_2)_pL^3(R^c)_q$ atoms or groups, where $L^2$, $L^3$, p and q are as previously defined and $R^c$ is as previously defined but is other than a hydrogen atom when $L^2$ and $L^3$ is each a covalent bond and p is zero.

Optionally substituted heteroaromatic groups, represented by the group $R_1$ in compounds of formulae (1) and (1a) include for example optionally substituted $C_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example nine- to thirteen-membered fused-ring heteroaromatic groups containing one, two or more heteroatoms selected from oxygen, sulphur or nitrogen atoms.

Particular examples of heteroaromatic groups of these types include optionally substituted pyrrolyl, furyl, thienyl, imidazolyl, N-$C_{1-6}$aimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, (2,3-dihydro]-benzofuryl, benzothienyl, benzotriazolyl, indolyl, isoindolyl, benzimidazolyl, imidazo[1,2-alpyridyl, benzothiazolyl, benzoxazolyl, benzopyranyl, [3,4-dihydro] benzopyranyl, quinazolinyl, naphthyridinyl, pyrido[3,4-b] pyridyl, pyrido[3,2-b]pyridyl, pyrido[4,3-b]pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Optional substituents which may be present on $R^1$ heteroaromatic groups include one, two, three or more —$L^2$ (CH$_2$)$_p$L$^3$(R$^c$)$_q$ atoms or groups as just defined.

Examples of the substituents represented by $R^a$ and $R^b$ in compounds of formula (1) and which may be present on aromatic or heteroaromatic groups represented by $R^1$ include atoms or groups —$L^2$(CH$_2$)$_p$LR$^c$, —$L^2$(CH$_2$)$_p$R$^c$, —$L^2R^c$, —(CH$_2$)$_p$R$^c$ and R$^c$ wherein $L^2$, (CH$_2$)$_p$, L and R$^c$ are as defined above. Particular examples of such substituents include —$L^2$CH$_2$L$^2$R$^c$, —$L^2$CH(CH$_3$)L$^3R^c$, —$L^2$(CH$_2$)$_2$L$^3R^c$, —$L^2$CH$_2R^c$, —$L^2$—$L^2$(CH$_2$)$_2R^c$, —CH$_2R^c$, —CH(CH$_3$)R$^c$ and —(CH$_2$)$_2R^c$ groups.

Thus each of $R^a$ and $R^b$ and, where present, substituents on $R^1$ and aromatic or heteroaromatic groups in compounds of the invention may be for example selected from a hydrogen atom, a halogen atom, e.g. a fluorine, chlorine, bromine or iodine atom, or a $C_{1-6}$alkyl, e.g. methyl, ethyl, n-propyl, i- propyl, n-butyl or t-butyl, $C_{1-6}$alkylamino, e.g. methylamino or ethylamino, $C_{1-6}$hydroxyalkyl, e.g. hydroxymethyl, hydroxyethyl or —C(OH)(CF$_3$)$_2$, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxypropylthio, $C_{1-6}$alkoxy, e.g. methoxy or ethoxy, hydroxy$C_{1-6}$alkoxy, e.g. 2-hydroxyethoxy, halo$C_{1-6}$alkyl, e.g. —CF$_3$, —CHF$_2$, CH$_2$F, halo$C_{1-6}$alkoxy, e.g. —OCF$_3$,—OCHF$_2$,—OCH$_2$F, $C_{1-6}$alkylamino, e.g. methylamino or ethylamino, amino (—NH$_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, isopropylaminoethoxy, or dimethylaminopropoxy, nitro, cyano, amidino, hydroxyl (—OH), formyl (HC(O)—], carboxyl (—CO$_2$H), —CO$_2R^{12}$, $C_{1-6}$alkanoyl e.g. acetyl, thiol (—SH), thio$C_{1-6}$alkyl, e.g. thiomethyl or thioethyl, sulphonyl (—SO$_3$H), $C_{1-6}$alkylsulphonyl, e.g. methylsulphonyl, aminosulphonyl (—SO$_2$NH$_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—CONH$_2$), C$_{1-6}$alkylaminocarbonyl, e.g. methylaminocarbonyl or ethylaminocarbonyl, C$_{1-6}$dialkylaminocarbonyl, e.g. dimethylaminocarbonyl or diethylaminocarbonyl, aminoC$_{1-6}$alkylaminocarbonyl, e.g. aminoethylaminocarbonyl, C$_{1-6}$dialkylaminoC$_{1-6}$alkylaminocarbonyl, e.g. diethylaminoethylaminocarbonyl, aminocarbonylamino. C$_{1-6}$alkylaminocarbonylamino, e.g. methylaminocarbonylamino or ethylaminocarbonylamino, C$_{1-6}$dialkylaminocarbonylamino, e.g. dimethylaminocarbonylamino or diethylaminocarbonylamino, C$_{1-6}$alkylaminocabonylC$_{1-6}$alkylamino, e.g. methylaminocarbonylmethylamino, aminothiocarbonylamino, C$_{1-6}$alkylaminothiocarbonylamino, e.g. methylaminothiocarbonylamino or ethylaminothiocarbonylamino, C$_{1-6}$dialkylaminothiocarbonylamino, e.g. dimethylaminothiocarbonylamino or diethylaminothiocarbonylamino, C$_{1-6}$alkylaminothiocarbonylC$_{1-6}$alkylamino, e.g. ethylaminothiocarbonylmethylamino, C$_{1-6}$alkylsulphonylamino, e.g. methylsulphonylamino or ethylsulphonylamino, C$_{1-6}$dialkylsulphonylamino, e.g. dimethylsulphonyl-amino or diethylsulphonylamino, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, C$_{1-6}$alkanoylamino, e.g. acetylamino, aminoC$_{1-6}$alkanoylamino e.g. aminoacetylamino, C$_{1-6}$dialkylaminoC$_{1-6}$alkanoylamino, e.g. dimethylaminoacetylamino, C$_{1-6}$alkanoylaminoC$_{1-6}$alkyl, e.g. acetylaminomethyl, C$_{1-6}$alkanoylaminoC$_{1-6}$alkylamino, e.g. acetamidoethylamino, C$_{1-6}$alkoxycarbonylamino, e.g. methoxycarbonylamino, ethoxycarbonylamino or t-butoxycarbonylamino group.

Aromatic groups represented by the group Ar in compounds of formulae (1) and (1a) include optionally substituted monocyclic of bicyclic fused ring C$_{1-6}$ aromatic groups. Particular examples include optionally substituted phenyl, 1- or 2-naphthyl, 1- or 2- tetrahydronaphthyl, indanyl or indenyl groups.

Optional substituents present on the aromatic groups represented by Ar include one, two, three or more substituents, each selected from an atom or group R$^6$ in which R$^6$ is —R$^{6a}$ or —Alk$^3$(R$^{6a}$)$_m$, where R$^{6a}$ is a halogen atom, or an amino (—NH$_2$), substituted amino, nitro, cyano, amidino, hydroxyl (—OH), substituted hydroxyl, formyl, carboxyl (—CO$_2$H), esterified carboxyl, thiol (—SH), substituted thiol, —COR$^7$ [where R$^7$ is an —Alk$^3$(R$^{6a}$)$_m$, aryl or heteroaryl group], —CSR$^7$, —SO$_3$H, —SO$_2$R$^7$ —SO$_2$NH$_2$, —SO$_2$NHR$^7$ SO$_2$N(R$^7$)$_2$, —CONH$_2$, —CSNH$_2$, —CONHR$^7$, —CSNHR$^7$, —CON[R$^7$]$_2$, —CSN(R$^7$)$_2$, —N(R$^4$)SO$_2$R$^7$, —N(SO$_2$R$^7$)$_2$, —NH(R$^4$)SO$_2$NH$_2$, —N(R$^4$)SO$_2$NHR$^7$, —N(R$^4$)SO$_2$N(R$^7$)$_2$, —N(R$^4$)COR$^7$, —N(R$^4$)CON(R$^7$)$_2$, —N(R$^4$)CSN(R$^7$)$_2$, —N(R$^4$)CSR$^7$, —N(R$^4$)C(O)OR$^7$, —SO$_2$NHet$^1$ [where —NHet$^1$ is an optionally substituted C$_{5-7}$cyclicamino group optionally containing one or more other —O— or —S— atoms or —N(R$^4$)—, —C(O)— or —C(S)— groups], —CONHet$^1$, —CSNHet$^1$, —N(R$^4$)SO$_2$NHet$^1$, —N(R$^4$)CONHet$^1$, —N(R$^4$)CSNHet$^1$, —SO$_2$N(R$^4$)Het$^2$ [where Het$^2$ is an optionally substituted monocyclic C$_{5-7}$carbocyclic group optionally containing one or more —O— or —S— atoms or —N(R$^4$)—, —C(O)— or —C(S)— groups], —CON(R$^4$) Het$^2$, —CSN(R$^4$)Het$^2$, —N(R$^4$)CON(R$^4$)Het$^2$,—N(R$^4$)CSN (R$^4$)Het$^2$, aryl or heteroaryl group; Alk$^3$ is a straight or branched C$_{1-6}$alkylene, C$_{2-6}$alkenylene or C$_{2-6}$alkynylene chain, optionally interrupted by one, two or three —O— or —S— atoms or —S(O)$_n$ [where n is an integer 1 or 2] or —N(R$^8$)—groups [where R$^8$ is a hydrogen atom or C$_{1-6}$alkyl, e.g. methyl or ethyl group]; and m is zero or an integer 1, 2 or 3. It will be appreciated that when two R$^4$ or R$^7$ groups are present in one of the above substituents, the R$^4$ or R$^7$ groups may be the same or different.

When in the group —Alk$^3$(R$^{6a}$)$_m$ m is an integer 1, 2 or 3, it is to be understood that the substituent or substituents R$^{6a}$ may be present on any suitable carbon atom in —Alk$^3$. Where more than one R$^{6a}$ substituent is present these may be the same or different and may be present on the same or different atom in —Alk$^3$. Clearly, when m is zero and no substituent R$^{6a}$ is present the alkylene, alkenylene or alkynylene chain represented by Alk$^3$ becomes an alkyl, alkenyl or alkynyl group.

When R$^{6a}$ is a substituted amino group it may be for example a group —NHR$^7$ [where R$^7$ is as defined above] or a group —N(R$^7$)$_2$ wherein each R$^7$ group is the same or different.

When R$^{6a}$ is a halogen atom it may be for example a fluorine, chlorine, bromine, or iodine atom.

When R$^{6a}$ is a substituted hydroxyl or substituted thiol group it may be for example a group —OR$^7$ or a —SR$^7$ or —SC(=NH)NH$_2$ group respectively.

Esterified carboxyl groups represented by the group R$^{6a}$ include groups of formula —CO$_2$Alk$^4$ wherein Alk$^4$ is a straight or branched, optionally substituted C$_{1-8}$alkyl group such as a methyl, ethyl, n-propyl, i-propyl, n-butyl, i-butyl, s-butyl or t-butyl group; a C$_{6-12}$arylC$_{1-8}$alkyl group such as an optionally substituted benzyl, phenylethyl, phenylpropyl, 1-naphthylmethyl or 2-naphthylmethyl group; a C$_{6-12}$aryl group such as an optionally substituted phenyl, 1-naphthyl or 2-naphthyl group; a C$_{6-12}$aryloxyC$_{1-8}$ alkyl group such as an optionally substituted phenyloxymethyl, phenyloxyethyl, 1-naphthyl-oxymethyl, or 2-naphthyloxymethyl group; an optionally substituted C$_{1-8}$alkanoyloxyC$_{1-8}$alkyl group, such as a pivaloyloxymethyl, propionyloxyethyl or propionyloxypropyl group; or a C$_{6-12}$aroyloxyC$_{1-8}$alkyl group such as an optionally substituted benzoyloxyethyl or benzoyloxypropyl group. Optional substituents present on the Alk$^4$ group include R$^{6a}$ substituents described above.

When Alk$^3$ is present in or as a substituent it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N(R$^8$)— groups.

Aryl or heteroaryl groups represented by the groups R$^{6a}$ or R$^7$ include mono- or bicyclic optionally substituted C$_{6-12}$ aromatic or C$_{1-9}$ heteroaromatic groups as described above for the groups R$^1$ and Het. The aromatic and heteroaromatic groups may be attached to the remainder of the compound of formula (1) by any carbon or hetero e.g. nitrogen atom as appropriate.

When —NHet$^1$ or —Het$^2$ forms part of a substituent R$^6$ each may be for example an optionally substituted pyrrolidinyl, pyrazolidinyl, piperazinyl, morpholinyl, thiomorpholinyl, piperidinyl or thiazolidinyl group. Additionally Het$^2$ may represent for example, an optionally substituted cyclopentyl or cyclohexyl group. Optional substituents which may be present on -NHet$^1$ or —Het$^2$ include those R$^5$ substituents described above.

Particularly useful atoms or groups represented by R$^6$ include fluorine, chlorine, bromine or iodine atoms, or $C_{1-6}$alkyl, e.g. methyl, ethyl, n-propyl, i-propyl, n-butyl or t-butyl, optionally substituted phenyl, pyridyl, pyrrolyl, furyl, thiazolyl, or thienyl, $C_{1-6}$alkylamino, e.g. methylamino or ethylamino, $C_{1-6}$hydroxyalkyl, e.g. hydroxymethyl or hydroxyethyl, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxy—propylthio, $C_{1-6}$alkoxy, e.g. methoxy or ethoxy, hydroxy$C_{1-6}$alkoxy, e.g. 2-hydroxyethoxy, optionally substituted phenoxy, pyridyloxy, thiazolyoxy, phenylthio or pyridylthio, $C_{5-7}$cycloalkoxy, e.g. cyclopentyloxy, halo$C_{1-6}$alkyl, e.g. trifluoromethyl, halo$C_{1-6}$alkoxy, e.g. trifluoromethoxy, $C_{1-6}$alkylamino, e.g. methylamino or ethylamino, amino (—$NH_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylamino ethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, isopropylaminoethoxy, or dimethylaminopropoxy, imido, such as phthalimido or naphthalimido, e.g. 1,8-naphthalimido, nitro, cyano, amidino, hydroxyl (—OH), formyl [HC(O)—], carboxyl (—$CO_2H$), —$CO_2Alk^4$ [where $Alk^4$ is as defined above], $C_{1-6}$ alkanoyl e.g. acetyl, optionally substituted benzoyl, thiol (—SH), thio$C_{1-6}$alkyl, e.g. thiomethyl or thioethyl, —SC(=NH)$NH_2$, sulphonyl (—$SO_3H$), $C_{1-6}$alkylsulphonyl, e.g. methylsulphonyl, aminosulphonyl (—$SO_2NH_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—$CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$dialkylamino$C_{1-6}$alkylamino—carbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, —CONHC(=NH)$NH_2$, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, optionally substituted phenylsulphonylamino, aminosulphonylamino (—$NHSO_2NH_2$), $C_{1-6}$alkylaminosulphonylamino, e.g. methylaminosulphonyl-amino or ethylaminosulphonylamino, $C_{1-6}$dialkylaminosulphonylamino, e.g. dimethylaminosulphonylamino or diethylaminosulphonylamino, optionally substituted morpholinesulphonylamino or morpholinesulphonyl$C_{1-6}$alkylamino, optionally substituted phenylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoyl-amino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino. ethoxycarbonylamino or t-butoxycarbonylamino or optionally substituted benzyloxy, pyridylmethoxy, thiazolylmethoxy, benzyloxycarbonylamino, benzyloxycarbonylamino$C_{1-6}$alkyl e.g. benzyloxycarbonylaminoethyl benzothio: pyridylmethylthio or thiazolylmethylthio groups.

Where desired, two $R^6$ substituents may be linked together to form a cyclic group such as a cyclic ether, e.g. a $C_{1-6}$alkylenedioxy group such as methylenedioxy or ethylenedioxy.

It will be appreciated that where two or more $R^6$ substituents are present, these need not necessarily be the same atoms and/or groups. In general, the substituent(s) may be present at any available ring position in the heteroaromatic group represented by Het.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates, e.g. p-toluenesulphonates, besylates or napsylates, phosphates, sulphates, hydrogen sulphates, acetates, trifluoroacetates, propionates, citrates, maleates. fumarates, malonates, succinates, lactates, oxalates, tartrates and benzoates.

Salts derived from inorganic or organic bases include alkali metal salts such as sodium or potassium salts, alkaline earth met al salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

R in compounds of the invention is preferably a —$CO_2H$ group.

When present, the aliphatic chain represented by $Alk^1$ in compounds of the invention is preferably a —$CH_2$— chain.

$Alk^2$ in compounds of formula (1) is preferably a —$CH_2$— chain and m is preferably an integer 1. In compounds of this type, the carbon atom to which $Alk^2$ and R are attached forms a chiral centre and is preferably in the L configuration.

$R^2$ in compounds of formula (1) is preferably a hydrogen atom.

$R^3$ in compounds of the invention is preferably a hydrogen atom.

In general in compounds of the invention —$(Alk^1)_n(L^1)_s$— is preferably $CH_2O$—, —$SO_2NH$, —C(O)O— or —CON($R^4$)— and is especially —CONH—.

In general in compounds of the invention the group $R^1$ is preferably an optionally substituted aromatic or heteroaromatic group. Particularly useful groups of these types include optionally substituted phenyl, pyridyl or pyrimidinyl groups, particularly those in which the substituent when present is an atom or group —$L^2(CH_2)_pL^3(R^c)_q$ as described above. Each substituent may be present on any available ring carbon or nitrogen atom.

The aromatic group represented by Ar in compounds of formulae (1) and (1a) is preferably on optionally substituted phenyl group. Each optional substituent when present is preferably an atom or group $R^6$ as defined above.

A particularly useful class of compounds according to the invention has the formula (1b)

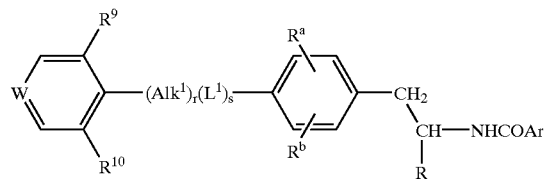
(1b)

wherein —W═ is —CH═ or —N═, $R^9$ and $R^{10}$, which may be the same or different, is each a —$L^2(CH_2)_pL^3(R^c)_q$ atom or group as generally and particularly defined above, and $Alk^1$, r, $L^1$, s, $R^a$, $R^b$, R and Ar are as generally and particularly defined above, and the salts, solvates, hydrates and N-oxides thereof.

It will be appreciated that the various preferences stated above in relation to groups present in compounds of formulae (1) and (1a) apply equally to the same groups when present in compounds of formula (1b).

Additionally, in compounds of formula (1b) —$(Alk^1)_r$—$(L^1)_s$— is preferably a —$CH_2O$ or —$CON(R^4)$— group and is especially a —CONH— group.

Ar is preferably an optionally substituted phenyl group. Particularly useful compounds of formula (1b) are those wherein Ar is a 2-, 3- or 4-monosubstituted or a 2,6-disubstituted phenyl group.

One of $R^9$ or $R^{10}$ in compounds of formula (1a) may be for example a hydrogen atom and the other a substituent $L^2(CH_2)_pL^3(R^c)_q$ in which $R^c$ is not a covalent bond and p is zero, but preferably each of $R^9$ and $R^{10}$ is a substituent —$L(^2CH_2)_pL^3(R^c)_q$ where $R^c$ is as just defined. Particularly useful $R^9$ or $R^{10}$ substituents include a hydrogen atom or halogen atom, especially fluorine or chlorine atoms, or a methyl, ethyl, methoxy, ethoxy, —$CF_3$, —OH, —CN, —$NO_2$, —$NH_2$, —$NHCH_3$, —$N(CH_3)_2$, —$COCH_3$, —$SCH_3$, —$CO_2H$ or —$CO_2CH_3$ group.

Particularly useful compounds according to the invention include the following:

(N-2,6-Dimethoxybenzoyl)-[O-(3,5-dichloro-4-pyridinyl)methyl]-L-tyrosine; 2-Carboxybenzoyl-(N'-3,5-dichloroisonicotinoyl)-L-4-aminophenylalanine;

(N-2,6-Dimethoxybenzoyl)-(N'-3,5-dichloroisonicotinoyl)-L-4-aminophenylalanine;

(N-3-Carboxybenzoyl)-(N'-3,5-dichloroisonicotoninoyl)-L-4-aminophenyalanine;

(N-4-Carboxybenzoyl)-(N'-3,5-dichloroisonicotinoyl)-L-4-aminophenylalanine;

(N-2-t-Butoxycarbonylbenzoyl)-(N'-3,5-dichloroisonicotinoyl)-L-4-aminophenylalanine;

(N-3-Cyanobenzoyl)-(N'-3,5-dichloroisonicotinoyl)-L-4-aminophenylalanine;

[N-3-(1-H-Tetrazol-5-yl)benzoyl]-(N'-3,5-dichloroisonicotinoyl)-L-4-aminophenylalanine;

[N-(3-Methoxycarbonylbenzoyl)]-(N'-3,5-dichloroisonicotinoyl)-L-4-aminophenylalnine;

and the salts, solvates, hydrates and N-oxides thereof.

The compounds of formulae (1), (1a) and (1b) may be prepared by a number of processes as generally described below and more specifically in the Examples hereinafter. In the following process description, the symbols $R^1$–$R^3$, $L^1$, $Alk^1$, $R^a$, $R^b$, $Alk^2$, m, r, s and Ar when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of the desired compound and the processes described hereinafter are to be understood to extend to such removal of protecting groups. For convenience, the processes described below all refer to the preparation of a compound of formula (1) but clearly the description applies equally to the preparation of compounds of formulae (1a) and (1b).

Thus a compound of formula (1) may be obtained by hydrolysis of an ester of formula (2):

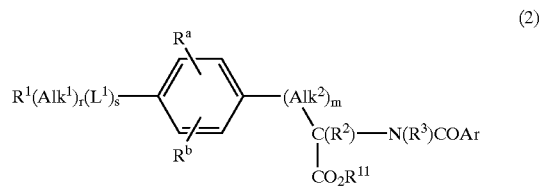
(2)

where $R^{11}$ is an alkyl group.

The hydrolysis may be performed using either an acid or a base depending on the nature of $R^9$, for example an organic acid such as trifluoroacetic acid or an inorganic base such as lithium hydroxide optionally in an aqueous organic solvent such as an amide, e.g. a substituted amide such as dimethylformamide, an ether, e.g. a cyclic ether such as tetrahydrofuran or dioxane or an alcohol, e.g. methanol at around ambient temperature. Where desired, mixtures of such solvents may be used.

Esters of formula (2) may be prepared by coupling an amine of formula 3):

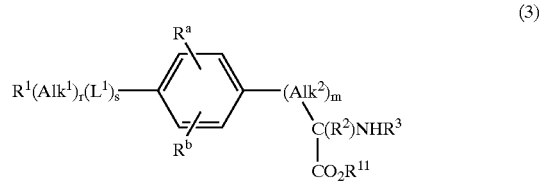
(3)

(where $R^{11}$ is as just described) or a salt thereof with an acid of formula (4):

$ArCO_2H$ (4)

or an active derivative thereof.

Active derivatives of acids of formula (4) include anhydrides, esters and halides. Particular esters include pentafluorophenyl or succinyl esters.

The coupling reaction may be performed using standard conditions for reactions of this type. Thus for example the reaction may be carried out in a solvent, for example an inert organic solvent such as an amide, e.g. a substituted amide such as dimethylformamide, an ether, e.g. a cyclic ether such as tetrahydrofuran, or a halogenated hydrocarbon, such as dichloromethane, at a low temperature, e.g. around −30° C. to around ambient temperature, optionally in the presence of a base, e.g. an organic base such as an amine, e.g. triethylamine, pyridine, or dimethylaminopyridine, or a cyclic amine, such as N-methylmorpholine.

Where an acid of formula (4) is used, the reaction may additionally be performed in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole. Alternatively, the acid may be reacted with a chloroformate, for example ethylchloroformate, prior to reaction with the amine of formula (3).

Intermediates of formulae (2), (3) and (4), or compounds of formula (1), may be manipulated to introduce substituents to aromatic or heteroaromatic groups or modify existing substituents in groups of these types. Typically, such manipulation may involve standard substitution approaches employing for example alkylation, arylation, heteroarylation, acylation, thioacylation, halogenation, sulphonylation, nitration, formylation or coupling reactions. Alternatively, exisitng substituents may be modified for example by oxidation, reduction or cleavage reactions. Particular examples of such reactions are given below. Where these are paticularly described in relation to the generation of the group $R^1(Alk^1)_r(L^1l)_s$—, it will be appreciated that each reaction may also be used to introduce or modify $R^5$ and/or $R^6$ substituents in for example Ar groups as appropriate.

Thus in one example, a compound wherein $R^1(Alk^1)_r(L^1)_s$— is a —$L^1H$ group may be alkylated, arylated or heteroaryiated using a reagent $R^1(Alk^1)_rX$ in which $R^1$ is other than a hydrogen atom and X is a leaving atom or group such as a halogen atom, e.g. a fluorine, bromine, iodine or chlorine atom or a sulphonyloxy group such as an alkylsulphonyloxy, e.g. trifluoromethylsulphonyloxy or arylsulphonyloxy, e.g. p-toluenesulphonyloxy group, The reaction may be carried out in the presence of a base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran.

In another example, a compound where $R^1(Alk^1)_r(L^1)_s$ is a —$L^1H$ group is a hydrogen atom may be functionalised by acylation or thioacylation, for example by reaction with a reagent $R^1(Alk^1)_rL^1X$ [wherein $L^1$ is a —C(O)—, C(S)—, —N($R^4$)C(O)— or N($R^4$)C(S)— group], in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature, or by reaction with $R^1(Alk^1)_rCO_2H$, $R^1(Alk)_4COSH$ or an activated derivative thereof, for example as described above for the preparation of esters of formula (2).

In a further example a compound may be obtained by sulphonylation of a compound where $R^1(Alk^1)_r(L^1)_s$ is an —OH group by reaction with a reagent $R^1(Alk^1)_rL^1Hal$ [in which $L^1$ is —S(O)— or —$SO_2$—and Hal is a halogen atom such as chlorine atom] in the presence of a base, for example an inorganic base such as sodium hydride in a solvent such as an amide, e.g. a substituted amide such as dimethylformamide at for example ambient temperature.

In another example, a compound where $R^1(Alk^1)_r(L^1)_s$ is a —$L^1H$ group, may be coupled with a reagent $R^1$ OH (where $R^1$ is other than a hydrogen atom) or $R^1Alk^1$ OH in a solvent such as tetrahydrofuran in the presence of a phosphine, e.g. triphenylphosphine and an activator such as diethyl, diisopropyl- or dimethylazodicarboxylate to yield a compound containing a $R^1(Alk^1)_rO$— group.

In a further example, ester groups —$CO_2R^4$ or —$CO_2Alk^4$ in compounds of formula (1) may be converted to the corresponding acid [—$CO_2H$] by acid- or base-catalysed hydrolysis depending on the nature of the grousp $R^4$ or $Alk^4$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxane or an alkali metal hydroxide, e.g. lithium hydroxide in an aqueous alcohol, e.g. aqueous methanol.

In a second example, —$OR^7$ [where $R^7$ represents an alkyl group such as methyl group] groups in compounds of formula (1) may be cleaved to the corresponding alcohol —OH by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding —$OCH_2R^7$ group (where $R^7$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [—$CO_2Alk^4$ or $CO_2R^4$] or aldehyde [—CHO] by reduction, using for example a complex metal hydride such as lithium aluminium hydride or sodium borohydride in a solvent such as methanol.

In another example, alcohol —OH groups in compounds of formula (1) may be converted to a corresponding —$OR^3$ group by coupling with a reagent $R^7OH$ in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NH_2$] groups in compounds of formula (1) may be obtained, in another example, by reaction of a corresponding amine [—$NH_2$] with sulphamide in the presence of an organic base such as pyridine at an elevated temperature, e.g. the reflux temperature.

In a further example amine (—$NH_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine [—$NH_2$] groups in compounds of formula (1) may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

Aromatic halogen substituents in compounds of the invention may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyldisulphide as the electrophile.

In another example, sulphur atoms in compounds of the invention, for example when present in the linker group $L^1$ may be oxidised to the corresponding sulphoxide using an oxidising agent such as a peroxy acid, e.g. 3-chloroperoxybenzoic acid, in an inert solvent such as a halogenated hydrocarbon, e.g. dichloromethane, at around ambient temperature. Intermediates of formulae (3) and (4), $R^1(Alk^1)_rX$, $R^1(Alk^1)_rL^1X$, $R^1(Alk^1)_rCO_2H$, $R^1OH$ and $R^1Alk^1OH$ for use in the above processes are either known compounds or may be prepared from known starting materials by use of analogous processes to those used for the preparation of the known compounds and/or by treating known compounds by one or more of the alkylation, acylation and other manipulations described herein, such as particularly described for the preparation of the Intermediates in the exemplification section hereinafter.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suit able solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racem ate of formula (1) may be separated using chiral High Performance Liquid Chromatography. Alternatively. if desired a particular enantiomer may be obtained by using an appropriate chiral intermediate in one of the processes described above.

The following Examples illustrate the invention. All temperatures are in ° C. The following abbreviations are used:
EDC-1-(3-dimethylaminopropyl)3-ethycarbodiimide;
DMF-dimethylformamide
HOBT-1-hydroxybenzotriazole;
NMM-N-methylmorpholine;
Ph-phenyl
EtOAc-ethyl acetate,
Ar-aryl;
$Et_2O$-diethylether;
DMSO-dimethylsulphoxide
THF-tetrahydrofuran,
DCM-dichloromethane,
Boc-tert-butoxycarbonyl
MeOH-methanol,
Me-methyl;
EtOH-ethanol,

INTERMEDIATE 1

N-(2,6-Dimethoxybenzoyl)-(O-benzyl)-L-tyrosine Methyl Ester

EDC (212 mg, 1.1 mmol) was added to a solution of (O-benzyl)tyrosine methyl ester hydrochloride (322 mg, 1 mmol), 2,6-dimethoxybenzoic acid (182 mg, 1 mmol), HOBT (149 mg, 1.1 mmol) and NMM (242 µl, 2.2 mmol) in DCM (10 ml). The mixture was stirred at room temperature overnight, then diluted with DCM (100 ml), washed with 10% citric acid (20 ml), saturated sodium bicarbonate solution (20 ml) and brine (20 ml), dried ($Na_2SO_4$) and evaporated under reduced pressure. The residue was purified by column chromatography ($SiO_2$; EtOAc/hexane, 60:40) to give the title compound as a colourless gum (392 mg, 87%). δH ($CDCl_3$) 7.44–7.31 (5H, m, $OCH_2Ph$), 7.29 (1H, t, 18.4 Hz, Ar(OMe)H), 7.14 (2H, d, 18.7 Hz, $CH_2Ar(O)H$), 6.88 (2H, d, J 8.7 Hz, $CH_2Ar(O)H$), 6.55 (2H, d, J 8.4 Hz, Ar(OMe)H), 6.36 (1H, br d, 17.4 Hz, CONH), 5.11 (1H, dt, J 7.5, 5.2 Hz, CHαtyr) 5.02 (2H, s, $OCH_2Ph$), 3.80 (6H, s, 2×ArOMe), 3.72 (3H, s, $CO_2Me$), 3.29 (1H, dd, J 5.5, 14.0 Hz. $CHCH_AH_BAr$) and 3.16 (1H, dd, J 4.9, 14.0 Hz, $CHCH_AH_BAr$); m/z (ESI, 15V) 450 (Mh⁺).

INTERMEDIATE 2

2-Thio(S-4-methylphenyl)benzoyl-(O-2,6-dichlorobenzyl)-L-tyrosine Methyl Ester

A solution of (O-2,6-dichlorobenzyl)-L-tyrosine methyl ester hydrochloride (0.39 g, 1 mmol), 2-thio(S-4-methylphenyl)benzoic acid (0.24 g, 1 mmol), EDC (0.21 g, 1.1 mmol), HOBT (0.16 g, 1.2 mmol) and NMM (0.28 ml; 0.25 g, 2.5 mmol) in DMF (5 ml) was stirred at room temperature for 16 h. The solvent was evaporated in vacuo and the residue partitioned between 10% hydrochloric acid (10 ml) and DCM (20 ml). The aqueous layer was extracted with DCM (20 ml) and the combined organic layers washed with $NaHCO_3$ solution (25 ml), dried over $MgSO_4$ and the solvent removed to give a brown oil that was purified by column chromatography ($SiO_2$; 2:5 EtOAc/hexane) to give an off-white solid that was recrystallised from EtOAc/hexane (1:2) to give the title compound as a white solid (0.24 g, 41%). δH ($CDCl_3$) 7.53–6.90 (15H,m ), 6.81 (1H, d, J 7.3 Hz), 5.22 (2H, s), 5.05 (1H, m), 3.77 (3H, s), 3.27 (1H, dd, J 5.9, 14.0 Hz), 3.18 (1H, dd, J 5.2, 14.0 Hz) and 2.35 (3H, s).

INTERMEDIATE 3

Methyl Phthalate

Solid sodium methoxide (5.4 g, 0.1 mmol) was added to a suspension of phthalic anhydride (14.8 g, 0.1 mmol) in MeOH (100 ml) and the reaction mixture stirred for 2 h at room temperature. The solvent was evaporated in vacuo, and the residue partitioned between DCM and 1.0M hydrochloric acid. The aqueous layer was extracted with DCM (2×20 ml), and the combined organic layers dried over $MgSO_4$. The solvent was removed to give the title compound as a white solid (17.3 g, 96%). δH ($CDCl_3$) 7.94–7.91 (1H, m), 7.70–7.63 (1H, m), 7.61–7.54 (2H, m) and 3.92 (3H, s).

INTERMEDIATE 4 a) 2-Methoxycarbonyl)benzoyl-(N-3,5-dichloroisonicotinoyl)-L-4-aminophenylalanine Methyl Ester Intermediate 3 (0.681 g, 3.78 mmol) was dissolved in dry DMF (20 ml) and (N-3,5-dichloroisonicotinoyl)-L-4-aminophenylalanine methyl ester hydrochloride (4 mmol; prepared from 3,5-dichloro-4-picoloyl chloride and N-Boc-L-4-aminophenylalanine methyl ester) added in one portion. To the mixture was added NMM (0.896 ml, 8.16 mmol), $HOBT.H_2O$ (0.551 g, 4.08 mmol) and EDC (0.783 g, 4.08 mmol). The reaction mixture was stirred under argon at room temperature for 2.5 h, poured into 50% saturated sodium bicarbonate solution (100 ml) and extracted with EtOAc (2×50 ml). The organic layer was washed with 50% saturated sodium bicarbonate solution (1×50 ml), 10% citric acid (1×50 ml), brine (1×50 ml), and dried over MgSO$_4$. The solvent was evaporated to give a white foam which was purified by chromatography (SiO$_2$; gradient elution DCM to DCM/MeOH (99:1)) to give the title compound as a white foam (1.0 g, 51%). δH (DMSO-d$^6$) 10.86 (1H, s), 8.92 (1H, d, J 7.9 Hz), 8.79 (2H, s), 7.70 (1H, dd, J 7.29, 1.3 Hz), 7.63–7.52 (4H, m), 7.37 (1H, dd, J 7.5, 1.3 Hz), 7.30 (2H, d, J 8.0 Hz), 4.66–4.58 (1H, m), 3.67 (3H, s), 3.363 (3H, s) and 3.15–2.95 (2H, m).

The following compound was prepared in a similar manner using 3-cyanobenzoic acid in place of Intermediate 3:
b) (N-3-Cyanobenzoyl)-(N'-3,5-dichloroisonicotinoyl)-L-4-aminophenylalanine Methyl Ester δH (CDCl$_3$) 8.55 (2H, s), 8.1–7.5 (7H, m), 7.12 (2H, d, J 8.5 Hz), 6.7 (1H, d, J 8.5 Hz), 5.15–5.05 (1H, m), 3.82 (3H, s) and 3.35–3.18 (2H, m). m/z (ES) 497 (MH$^+$).

Using a similar procedure to Intermediate 4a) employing the phenylalanine t-butyl ester in place of the corresponding methyl ester, the following compound was prepared:
c) [N-3-Methoxycarbonyl)benzoyl]-(N'-3,5-dichloroisonicotinoyl)-L-4-aminophenylalanine t-Butyl Ester δH (CDCl$_3$), 8.44 (2H, s), 7.92–7.2 (9H, m), 6.53 (1H, d, J 7.8 Hz), 4.99–4.93 (1H, m), 3.85 (3H, s), 3.23 (2H, d, J 5.6 Hz) and 1.46 (9H, s). m/z (ES) 572 (MH$^+$).

INTERMEDIATE 5

Benzyl-4-{2-[(diphenylmethylene)amino]-3-ethoxy-3-oxooropyl}benzoate

A mixture of benzyl-4-(bromomethyl)benzoate (7.61 g, 24.9 mmol), N-(diphenylmethylene)glycine ethyl ester (6.66 g, 24.9 mmol) and potassium carbonate (6.9 g, 50 mmol) in acetonitrile (300 ml) were heated to reflux for 20 h. The reaction was concentrated in vacuo, and the residue partitioned between EtOAc (100 ml) and water (100 ml). The aqueous layer was extracted with EtOAc (100 ml) and the combined organic layers were dried (Na$_2$SO$_4$), and concentrated in vacuo to give the title compound as a pale straw coloured oil (13.0 g) which was used without further purification. δH (CDCl$_3$) 7.90 (2H, d, J 8.3 Hz, Ar—H), 7.58 (2H, d, J 7.3 Hz, Ar—H), 7.50–7.25 (13H, m, Ar—H), 7.14 (2H, d, J 8.1 Hz, Ar—H), 6.65 (2H, d, J 6.8 Hz, CH$_2$Ph), 5.33 (2H, m, CHC$\underline{H}_2$Ar), 4.30–4.15 (3H, m, C$\underline{H}$CH$_2$Ar) and C$\underline{H}_2$CH$_3$) and 1.26 (3H, t, J 7.1 Hz. CH$_2$C$\underline{H}_3$). m/z (ESI, 60V) 492 (MH$^+$).

INTERMEDIATE 6

4-(Benzyloxycarbonyl)phenylalanine Ethyl Ester Hydrochloride

A solution of Intermediate 5 (13.0 g, 25 mmol) in THF (200 ml) was treated with hydrochloric acid (2.0M solution, 20 ml, 40 mmol) and stirred at room temperature for 2 h. then concentrated in vacuo and triturated with Et$_2$O to give a white solid which was purified by recrystallistion from EtOH/EtOAc to give the title compound as a white solid (4.24 g, 47%). δH (DMSO-d$^6$) 7.96 (2H, dd, J 6.6, 1.7 Hz, Ar—H), 7.48–7.37 (7H, 6m, Ar—H), 5.35 (2H, s, C$\underline{H}_2$Ph), 4.29 (1H, dd, J 7.7, 5.0 Hz, CHα), 4.11 (2H, q, J 7.1 Hz, C$\underline{H}_2$CH$_3$), 3.27 (1H, dd, J 14.0, 5.9 Hz, CHC$\underline{H}_A$H$_B$Ar), 3.15 (1H, dd, J 14.0, 7.7 Hz, CHCH$_A\underline{H}_B$Ar) and 1.08 (3H, t, J 7.1 Hz, CH$_2$C$\underline{H}_3$), m/z (ESI, 60V) 328 (MH$^+$).

INTERMEDIATE 7

(N-2,6-Dimethoxybenzovyl-4-(benzyloxycarbonyl)phenylalanine Ethyl Ester

A solution of Intermediate 6 (2.75 g, 8.4 mmol) and NMM (1.25 mg, 11.2 mmol) in DCM (50 ml) was treated with 2,6-dimethoxybenzoyl chloride (2.25 g, 11.2 mmol) and stirred for 16 h at room temperature. The solution was concentrated in vacuo and partitioned between dilute HCl (50 ml) and EtOAc (100 ml). The aqueous layer was extracted with EtOAc (2×50 ml) and the combined organic layers washed with water (100 ml) and NaHCO$_3$ solution (100 ml), dried (Na$_2$SO$_4$) and concentrated in vacuo to give the title compound as a pale amber glass (3.36 g, 82%) which was used without further purification. δH (CDCl$_3$) 7.96 (2H, d, J 8.4 Hz, Ar—H), 7.45–7.28 (8H, m, Ar—H), 6.56 (2H, d, J 8.4 Hz, Ar—H), 6.37 (1H, d, J 7.2 Hz, NH), 5.34 (2H, s, COC$\underline{H}_2$Ph), 5.13 (1H, m, CHα), 4.16 (2H, q, J 7.1 Hz, C$\underline{H}_2$CH$_3$), 3.80 (6H, s, OMe), 3.42 (1H, dd, J 13.8, 5.7 Hz, CHC$\underline{H}_A$H$_B$Ar), 3.26 (1H, dd, J 13.8, 4.9 Hz, CHCH$_A\underline{H}_B$Ar) and 1.25 (3H, t, J 7.1 Hz, CH$_2$C$\underline{H}_3$). m/z (ESI, 60V) 492 (MH$^+$).

INTERMEDIATE 8

(N-2,6-Dimethoxybenzoyl)-4-carboxyphenylalanine Ethyl Ester

A solution of Intermediate 7 (3.35 g, 6.8 mmol) in EtOH (300 ml) was treated with 10% palladium on charcoal (400 mg) and stirred under an atmosphere of H$_2$ for 20 h. The catalyst was removed by filtration through Celite® and the solution concentrated in vacuo to give the title compound as a glass (2.78 g, 100%). δH (CDCl$_3$) 7.99 (2H, d, J 8.2 Hz, Ar—H), 7.36 (2H: d, J 8.2 Hz, Ar—H), 7.27 (1H, t, J 8.4 Hz, Ar—H), 6.55 (2H, d, J 8.4 Hz, Ar—H), 6.42 (1H, d, J 7.3 Hz, NH), 5.15 (1H, m, CHα), 4.18 (2H, q, J 7.1 Hz, C$\underline{H}_2$CH$_3$), 3.81 (6H, s, OMe), 3.45 (1H, dd, J 13.7, 5.6 Hz, CHC $\underline{H}_A$H$_B$Ar), 3.28 (1H, dd, J 13.7, 6.9 Hz, CHCH$_A\underline{H}_B$Ar) and 1.26 (3H, t, J 7.1 Hz, CH$_2$C$\underline{H}_3$). m/z (ESI, 60V) 402 (MH$^+$).

INTERMEDIATE 9

(N-2,6-Dimethoxybenzoyl)-4-(benzylaminocarbonyl)phenylalanine Ethyl Ester

A solution of Intermediate 8 (0.73 g, 1.82 mmol) in DCM (40 ml) was treated with oxalyl chloride (5 ml) and DMF (1 drop) and stirred at room temperature for 2 h. The solvent was removed in vacuo and the residue azeotroped with toluene, dissolved in CCM (40 ml), and treated with benzylamine (1.0 ml) and stirred at room temperature for 3 h. The reaction was concentrated in vacuo and partitioned between dilute HCl (1.0M, 30 ml) and EtOAc (50 ml). The aqueous layer was extracted with EtOAc (3×50 ml) and the combined organic layers washed with NaHCO$_3$ solution (2×50 ml) and brine (50 ml), dried (Na$_2$SO$_4$) and concentrated in vacuo to give the title compound as a white solid (1.07 g) which was used without further purification. δH (CDCl$_3$) 7.75 (1H, br s, NH), 7.69 (2H, d, J 8.3 Hz, ArH), 7.38–7.24 (8H, m, Ar—H), 6.65 (2H, d, J 8.4 Hz, Ar—H), 6.36 (1H, d, J 6.9 Hz, Ar—H), 5.12 (1H, m, CHα), 4.63 (2H, d, J 5.6 Hz, NHC$\underline{H}_2$Ph), 4.16 (2H, q, J 7.1 Hz, C$\underline{H}_2$CH$_3$), 3.80 (6H, s, OMe), 3.40 (1H, dd, J 13.8, 5.8 Hz, CHC$\underline{H}_A$H$_B$Ar), 3.25 (1H, dd, J 13.8, 4.9 Hz, CHCH$_A\underline{H}_B$Ar) and 1.25 (3H, t, J 7.1 Hz, CH$_2$C$\underline{H}_3$). m/z (ESI, 60V) 491 (MH$^+$).

INTERMEDIATE 10

[N-3-(1-H-Tetrazol-5-yl)benzoyl]-(N'-3,5-dichloroisonicotinoyl)-L-4-aminophenylalanine Methyl ester To Intermediate 4b) (0.424 g, 0.85 mmol) in dry toluene (10 ml) was added trimethylsilyl azide (0.22 ml) and di-n- butyl tin oxide (21 mg). The solution was refluxed overnight, cooled and then evaporated. Chromatography on silica gel eluting with EtOAc hexane 50:50 afforded the title compound as a foam (0.214 g, 46%). δH (CD$_3$OD), 8.6 (2H, s), 8.4–7.42 (6H, m), 7.3 (2H, d, J 8.5 Hz), 4.92 (1H,m), 4.8 (3H, s) and 3.18–3.09 (2H, m). m/z (ES) 497 (MH$^+$).

INTERMEDIATE 11

3,5-Dichloro-4-hydroxymethylpyridine

A solution of 3,5-dichloropyridine-4-carboxaldehyde (1.34 g, 7.6 mmol) in MeOH (10 ml) was treated with NaBH$_4$ (0.29 g, 7.6 mmol) and stirred at room temperature for 2 h. The reaction was quenched with water (5 ml) and concentrated in vacuo. The residue was partitioned between EtOAc (20 ml) and 10% HCl (10 ml). The aqueous layer was extracted with EtOAc and the combined organic extracts, washed with 10% NaHCO$_3$ solution, dried (MgSO$_4$) and concentrated in vacuo to give the title compound as a white solid (1.05 g, 78%). δH (CDCl$_3$) 8.52 (2H, s, pyr-H), 4.94 (2H, br s, C$\underline{H}_2$OH) and 2.28 (1H, br s, OH).

INTERMEDIATE 12

3,5-Dichloro-4-bromomethylpyridine

A solution of Intermediate 11 (0.50 g, 2.80 mmol) in DCM (10 ml) was treated with thionyl bromide (3.51 g, 1.32 ml, 16.9 mmol) and heated to reflux for 3 h. The reaction was quenched with 10% NaHCO$_3$ solution (10 ml) and extracted with DCM (25 ml). The organic layer was dried (MgSO$_4$) and concentrated in vacuo to give the title compound as a yellow oil that solidified on standing (0.65 g, 96%) and was used without further purification. δH (CDCl$_3$) 8.50 (2H, s, pyr-H), 4.63 (2H, s, CH$_2$Br). m/z (ESI, 60V) 242 (MH$^+$).

EXAMPLE 1

N-(2,6-Dimethoxybenzoyl)-(O-benzyl)-L-tyrosine

Lithium hydroxide monohydrate (4.2 mg, 1 mmol) was added to a solution of Intermediate 1 (385 mg, 0.857 mmol) in THF (10 ml) and water (10 ml). The mixture was stirred for 1 h at room temperature. The THF was removed under reduced pressure, the aqueous residue acidified (dilute HCl aq.) and extracted with DCM (3×50 ml). The extracts were dried (Na$_2$SO$_4$) and evaporated under reduced pressure. The residue was freeze dried from a mixture of MeOH and water to give the title compound as a white fluffy solid (365 mg, 98%). δH (DMSO-d$^6$) 12.53 (1H, br s, CO$_2$H), 8.13 (1H, d, J 7.9 Hz, CONH), 7.45–7.30 (5H, m, OCH$_2$Ph), 7.25 (1H, t, J 8.4 Hz, Ar (OMe)$\underline{H}$), 7.18 (2H, d, J 8.6 Hz, CH$_2$Ar(O)$\underline{H}$), 6.92 (2H, d, J 7.5 Hz, CH$_2$Ar(O)$\underline{H}$), 6.61 (2H, d, J 8.4 Hz, Ar(OMe)$\underline{H}$), 5.07 (2H, s, OCH$_2$Ph), 4.51 (1H, dt, J 5.1, 8.3 Hz, CHαtyr), 3.63 (6H, s, 2×Ar(OMe)), 3.00 (1H, dd, J 5.1, 14.0 Hz, CHC$\underline{H}_A$H$_B$Ar) and 2.87 (1H, dd, J 8.6, 14.0 Hz, CHCH$_A\underline{H}_B$Ar); m/z (ESI, 15V) 436 (MH$^+$).

EXAMPLE 2 a) 2-Thio(S-4-methylphenyl)benzoyl-(O-2,6-dichlorobenzyl)-L-tyrosine

A solution of Intermediate 2 (0.24 g, 0.41 mmol) in THF (7.5 ml) and water (4.5 ml) was treated with lithium hydroxide monohydrate (26 mg, 0.62 mmol) and stirred at room temperature for 16 h. The reaction was acidified to pH1 with 10% hydrochloric acid and extracted with DCM (2×20 ml). The combined organic layers were dried over MgSO$_4$ and the solvent evaporated in vacuo to give a white solid which was triturated with EtOAc/hexane (1:1) to give the title compound (176 mg, 76%). δH (CDCl$_3$) 7.52 (1H, m), 7.34–7.14 (11H, m), 7.05 (1H, m), 6.90 (2H,m ), 5.18 (2H, s), 5.04 (1H, m), 3.34 (1H, dd, J 5.6, 14.2 Hz), 3.24 (1H, dd, J 5.7, 14.2 Hz) and 2.34 (3H, s). m/z (ES+, 60V), 566 (MH$^+$).

The following compounds were prepared in a similar manner from the corresponding esters produced in a similar manner to Intermediate 2:

b) (N-2-Chlorobenzoyl)-(O-2,6-dichlorobenzyl)-L-tyrosine

δH (DMSO-d$^6$), 8.71 (1H, d, J 8.2 Hz), 7.7–7.3 (7H, m), 7.23 (2H, d, J 8.4 Hz), 6.97 (2H, d, J 8.4 Hz), 4.58 (1H, m), 3.2–2.8 (2H, m). m/z 478 (MH$^+$)

c) (N-2,4,6-Trimethylbenzoyl)-(O-2,6-dichlorobenzyl)-L-tyrosine

δH (DMSO-d$^6$), 8.46 (1H, d, J 7.3 Hz), 7.65–7.4 (3H, m), 7.25 (2H, d, J 8.6 Hz), 6.95 (2H, d, J 8.6 Hz), 6.76 (2H, s), 5.19 (2H, s), 4.65 (1H, m), 3.3–3.05 (1H, m), 2.95–2.75 (1H, m), 2.19 (3H, s) and 1.93 (6H, s); m/z (ESI, 60V) 486 (MH$^+$).

d) (N-2,6-Dimethoxybenzoyl)-[O-3,5-dichloro-4-pyridinyl)methyl]-L-tyrosine

The tyrosine starting material for coupling with acid to produce the required ester for hydrolysis was obtained by reaction of Intermediate 12 with N-Boc-L-tyrosine methyl ester in the presence of sodium hydride.

δH (DMSO-d$^6$), 12.55 (1H, br s, CO$_2$H), 8.72 (2H,s, pyr H), 8.15 (1H, d, J 7.8 Hz, NH), 7.29–7.22 (3H, m, Ar—H), 6.98 (2H, d, J 8.6 Hz, Ar—H), 6.63 (2H, d, J 8.6 Hz, Ar—H), 5.21 (2H, s, CH$_2$O), 4.56 (1H, m, CHα), 3.65 (6H, s, OMe), 3.30–2.90 (2H, m, CHC$\underline{H}_2$Ar); m/z (ESI, 60V) 505 (MH$^+$).

e) N-2-Carboxybenzoyl-[O-(3,5-dichloro-4-pyridinyl)methyl]-L-tyrosine

δH (DMSO-d$^6$), 12.8 (1H, br s, CO$_2$H), 8.72 (2H, s, pyr-H), 8.63 (1H, d, J 8.0 Hz, NH), 7.72–7.69 (1H, m, Ar—H), 7.57–7.47 (2H, m, Ar—H), 7.31 (1H, m, Ar—H), 7.24 (2H, d, J 8.6 Hz, Ar—H), 6.97 (2H, d, J 8.6 Hz, Ar—H), 5.20 (2H, s, CH$_2$O), 4.55 (1H, m, CHα), 3.06–2.98 (2H, m, CHC$\underline{H}_2$Ar); m/z (ESI, 60V) 489 (MH$^+$).

EXAMPLE 3 a) 2-Carboxybenzoyl-(N'-3,5-dichloroisonicotinoyl)-L-4-aminophenylalanine

Intermediate 4 (0.5 g, 0.94 mmol) was treated with lithium hydroxide monohydrate (0.095 g, 2.26 mmol) in dioxane/H$_2$O (30 ml, 2:1). After 30 min. glacial acetic acid was added (1 ml) and the solvent removed in vacuo. Water was added to the residue and the white solid filtered, washed well with H$_2$O and dried in vacuo to give the title compound as a white solid (0.18 g, 38%). δH (DMSO-d$^6$) 10.84 (1H, s), 8.78 (2H, s), 8.68 (1H, d, J 7.2 Hz), 7.71 (1H, dd), 7.58–7.50 (4H, m), 7.36–7.29 (3H, m), 4.61–4.56 (1H, m) and 3.13–2.98 (2H, m).

The following compounds were prepared in a similar manner from the corresponding ester. Each ester was prepared using a similar procedure to that described for the preparation of Intermediate 4, using (N-3,5-dichloroisonicotinoyl)-L-4-aminophenylalanine methyl ester hydrochloride [see Intermediate 4] and the appropriate activated acid:

b) [N-(6-Carboxy-2-methoxy)benzoyl]-(N-3,5-dichloroisonicotinoyl)-L-4-aminophenylalanine δH (DMSO-d$^6$), 10.85(1H, s, CO$_2$H), 8.77 (2H, s,ArCl$_2$ $\underline{H}$), 8.22 (2H, d, J 7.8 Hz), 7.50–7.35 (2H, m), 7.35–7.20 (3H, m), 4.70–4.60 (1H, m, CH), 3.70 (3H, s, O$\underline{Me}$), and 3.01 (2H, d, J 6.9 Hz, CH$_2$); m/z (ESI, 60V) 532 (MH$^+$).

c) [N-(2-Phenoxy-6-carboxy)benzoyl]-(N'-3,5-dichloroisonicotinoyl)-L-4-aminophenylalanine δH (DMSO-d⁶), 10.82 (1H, s, CO₂H), 8.77 (2H,s, ArCl₂ H), 8.52 (1H, d, J 7.8 Hz), 7.64 (1H, d, J 7.7 Hz), 7.44 (2H, t, J 7.4 Hz), 7.36 (2H, t, J 7.9 Hz), 7.19 (2H, d, J 8.4 Hz), 7.12 (2H, t, J 7.13 Hz), 7.01 (2H, d, J 8.4 Hz), 4.68–4.61 (1H, m, CH) and 2.96 (2H, d, J 6.2 Hz, CH₂); m/z (ESI, 60V) 594 (MH⁺).

d) (N-2-Phenoxybenzoyl)-(N'-3,5-dichloroisonicotonoyl)-L-4-aminophenylalanine

δH (DMSO-d⁶), 10.78 (1H, br s, CO₂H) 8.77 (2H, s, ArCl₂H), 8.35 (1H, d, J 5.9 Hz), 7.92 (1H, dd, J 7.8, 1.8 Hz), 7.94–7.34 (6H, m, ArH), 7.21 (1H, t, J 7.5 Hz), 7.15 (1H, t, J 7.2 Hz), 7.02 (2H, d, J 8.6 Hz), 6.95 (2H, d, J 8.6 Hz), 6.84 (1H, d, J 8.2 Hz), 4.20–4.13 (1H, m, CH), 3.16 (1H, dd, J 13.0, 5.3 Hz, CH_AH_B) and 3.01 (1H, dd, J 13.0, 4.3 Hz, CH_A H_B); m/z (ESI, 60V) 550 (MH⁺).

e) [N-(2-Carboxy-6-methyl)benzoyl]-(N'-3,5-dichloroisonicotinoyl)-L-4-aminophenylalanine δH (DMSO-d⁶),8.78 (2H, s, ArCl₂H), 8.49 (1H, d, J 7.6 Hz), 7.69 (1H, d, J 7.0 Hz), 7.55 (2H, d, J 8.3 Hz), 7.40–7.20 (4H, m), 4.72–4.60 (1H, m, CH), 3.11–2.93 (3H, m, Me) and 2.10 (2H, s, CH₂); m/z (ESI, 60V) 516 (MH⁺).

f) (N-2,6-Dimethoxybenzovyl)-(N'-3,5-dichloroisonicotinoyl)-L-4-aminophenylalanine δH (DMSO-d⁶), 12.60 (1H, br s, NH), 10.86 (1H, s, NH), 8.79 (2H, s, pyr-H), 8.21 (1H, d, J 8.1 Hz, Ar—H), 7.58 (2H, d, J 8.5 Hz, Ar—H), 7.29 (2H, d, J 8.4 Hz, Ar—H), 6.63 (2H, d, J 8.4 Hz, Ar—H), 4.59 (1H, m, CHα), 3.66 (6H, s, OMe), 3.07 (1H, dd, J 13.8, 5.0 Hz, CHCH_AH_BAr) and 2.92 (1H, dd, J 13.8, 9.0 Hz, CHCH_AH_BAr); m/z (ESI, 60V) 518 (MH⁺).

g) (N-3-Carboxybenzoyl)-(N'-3,5-dichloroisonicotoninoyl)-L-4-aminophenyalanine

δH (DMSO-d⁶), 12.95 (1H, br s, CO₂H) 10.83 (1H, s, NH), 8.95 (1H, d, J 8.1 Hz, Ar—H), 8.77 (2H, s, pyr-H), 8.43 (1H, t, J 1.6 Hz, Ar—H), 8.06 (2H, m, Ar—H), 7.60 (1H, m, Ar—H), 7.55 (2H, d, J 8.5 Hz, Ar—H), 7.32 (2H, d: J 8.5 Hz, Ar—H), 4.64 (1H, m, CHα) and 3.10 (2H, m, CHC H₂Ar); m/z (ESI, 160V) 502 (MH⁺).

h) (N-4-Carboxybenzoyl)-(N'-3,5-dichloroisonicotinoyl)-L-4-aminophenylalanine

δH (DMSO-d⁶, 350K), 12,62 (1H, br s, CO₂H), 10.60 (1H, s, NH), 8.72 (2H, s, pyr-H), 8.56 (1H, d, J 7.9 Hz, NH), 8.01 (2H, d, J 8.4 Hz, Ar—H), 7.88 (2H, d, J 8.4 Hz, Ar—H), 7.55 (2H, d, J 8.4 Hz, Ar—H), 7.31 (2H, d, J 8.4 Hz, Ar—H), 4.70 (1H, m, CHα), 3.22 (1H, dd, J 14.0, 5.0 Hz, CHC H_AH_BAR) and 3.11 (1H, dd, J 14.0, 9.5 Hz, CHCH_AH_BAr); m/z (ESI, 160V), 502 (MH⁺).

i) (N-2-Carboxy-6-hydroxybenzoyl)-N'-3,5-dichloroisonicotinoyl)-L-4-aminophenylalanine δH (DMSO-d⁶), 10.84 (1H, s, NH), 8.87 (2H, s, pyr-H), 8.52 (1H, d, J 8.0 Hz, Ar—H), 7.56 (2H, d, J 8.3 Hz, Ar—H), 7.29–7.26 (3H, m, Ar—H), 6.94 (1H, d, J 8.3 Hz, Ar—H), 6.85 (1H, d, J 8.3 Hz, Ar—H), 4.454 (1H, m, CHα), 3.16–2.96 (2H, m, CHCH₂Ar); m/z (ESI, 60V) 518 (MH⁺).

j) (N-2-t-Butoxycarbonylbenzoyl)-(N'-3,5-dichloroisonicotinoyl)-L-4-aminophenylalanine δH (DMSO-d⁶), 10.84 (1H, s, NH), 8.78 (2H, s, pyr-H), 8.62 (1H, m, NH), 7.64–7.44 (5H, m, Ar—H), 7.39–7.20 (3H, m, Ar—H), 4.56 (1H, m, CHα), 3.16 (1H, m, CHC H_AH_BS), 3.09–2.94 (1H, m, CHCH_AH_BAr) and 1.36 (9H, s, ᵗBu); m/z (ESI, 60V) 580 (MH⁺).

EXAMPLE 4 a) (N-2,6-Dimethoxybenzoyl)-4-carboxamidobenzyl) phenylalanine

A solution of Intermediate 9 (1.07 g, 1.82 mmol) in 1,4-dioxane (100 ml) was treated with lithium hydroxide (168 mg, 4.0 mmol) and water (20 ml). The reaction was stirred at room temperature for 2 h then THF (50 ml) was added and stirring continued for a further 1 h. The reaction was concentrated in vacuo and the residue partitioned between EtOAc (50 ml) and water (50 ml). The aqueous layer was washed with EtOAc (50 ml) and the combined organic layers extracted with water (100 ml). The combined aqueous layers were acidified to pH 1 with 2.0M hydrochloric acid and extracted with EtOAc (3×50 ml). The combined organic layers were dried (Na₂SO₄) and concentrated in vacuo to give a white solid (0.96 g) which was purified by crystallisation from EtOAc/diisopropyl ether to give the title compound as a white solid (0.56 g, 66%). δH (DMSO-d⁶) 8.99 (1H, t, J 6.0 Hz, NH), 8.24 (1H, d, J 8.0 Hz, NH), 7.84 (2H, d, J 8.3, Ar—H), 7.38 (2H, d, J 8.3 Hz, Ar—H), 7.33–7.30 (5H, m, Ar—H), 7.26 (1H,t, J 8.4 Hz, Ar—H), 6.63 (2H, d, J 8.4 Hz, Ar—H), 4.62 (1H, m, CHα), 4.48 (2H, d, J 6.0 Hz, NHCH₂Ph), 3.64 (6H, s,OMe), 3.13 (1H, dd, J 14.0, 4.9 Hz, CHCH_AH_BAR) and 2.99 (1H, dd, J 14.0,9.0 Hz, CHCH_AH_BAr). m/z (ESI, 60V) 463 (MH⁺).

The following compounds were prepared in a similar manner to the compound of Example 4a) by hydrolysis of the corresponding ester. Each ester was prepared by reaction of Intermediate 8 with the amine shown using a similar procedure to that described for the preparation of Intermediate 9.

b) (N-2,6-Dimethoxybenzoyl)-4-[carboxamido(3,5-dichlorobenzyl)]-phenylalanine.

from Intermediate 8 and 3,5-dichloroaniline. δH (DMSO-d⁶, 390K), 10.46 (1H, s, NH), 8.27 (1H, d, J 8.0 Hz, NH), 7.91 (2H,d, J 1.9 Hz, Ar—H), 7.89 (2H, d, J 8.3 Hz, Ar—H), 7.46 (2H, d, J 8.3 Hz, Ar—H), 7.31 (1H, t, J 1.9 Hz, Ar—H), 7.26 (1H, t, J 8.4 Hz, Ar—H), 6.63 (2H, d, J 8.4 Hz, Ar—H), 4.64 (1H, m, CHα), 3.65 (6H, s, OMe), 3.17 (1H, dd, , 14.0, 5.1 Hz, CHCH_AH_BAr)), and 3.03 (1H, dd, J 14.0, 9.0 Hz, CHCH_AH_BAr). m/z (ESI, 60V) 518 (MH⁺).

c) (N-2,6-Dimethoxybenzoyl)-4-carboxamidomorpholyl)-phenylalanine from Intermediate 8 and morpholine. δH (DMSO-d⁶, 390K), 8.26 (1H, d, J 7.9 Hz, NH), 7.34 (4H, m, Ar—H), 7.26 (1H, t, J 8.4 HZ), 6.62 (2H, d, J 8.4 Hz, Ar—H), 4.61 (1H, m, CHα), 3.81–3.40 (8H, m, CH₂), 3.64 (6H, s, OMe), 3.11 (1H, dd, J 13.9, 4.75 Hz, CHCH_AH_BAr) and 2.98 (1H, dd, J 13.9, 9.0 Hz, CHCH_AH_BAR). m/z (ESI, 60V) 443 (MH⁺)

d) (N-2,6-Dimethoxybenzoyl)-4-(carboxamidodiethyl) phenylalanine from Intermediate 8 and diethylamine δH (DMSO-d⁶), 8.24 (1H, d, J 8.0 Hz, NH), 7.32 (5H, m, Ar—H), 6.63 (2H, d, J 8.4 Hz, Ar—H), 4.61 (1H, m, CHα), 4.11 (4H, m, C H₂CH₃), 3.65 (6H, s, OMe), 334–2.99 (2H, m, CHCH₂Ar) and 1.08 (6H, t, J 7.1 Hz, CH₂CH₃). m/z (ESI, 60V) 429 (MH⁺)

EXAMPLE 5

[N-(4-Phenyl)benzoyl]-[O-(3,5-dichloro-4-pyridinyl) methyl]-L-tyrosine

To 4-phenylbenzoyl-L-tyrosine (0.75 g, 2 mmol) and DMF (20 ml) in a flask under N₂ was added 2.1 equivalents of a 60% dispersion of NaH (0.168 g). This mixture was stirred at room temperature for 20 minutes followed by the addition of Intermediate 12 (0.484 g, 2 mmol). Stirring was continued for 2.5 h. The reaction was then quenched with aqueous NaHCO₃, the DMF was evaporated, EtOAc and water were added and a white solid appeared which was filtered and washed with water and Et₂O. The white solid was passed through a Dowex-56WX4-400 ion exchange resin, eluting with THF/acetonitrile [50:50] and freeze dried to afford the title compound as a white solid (0.3 g). δH (DMSO-d$^6$), 8.7 (2H, s), 7.95–7.35 (10H, m), 7.1 (2H, d, J 8.5 Hz), 6.85 (2H, d, J 8.5 Hz), 5.15 (2H, s), 4.15 (1H, br s) and 3.31–3.05 (2H, m). m/z 521 (MH$^+$)

EXAMPLE 6

(N-3-Cyanobenzoyl)-(N'-3,5-dichloroisonicotinoyl)-L-4-aminophenylalanine

To Intermediate 4b) (0.174 g, 0.35 mmol) in THF (5 ml) and water (5 ml) was added lithium hydroxide monohydride (22 mg). The reaction was stirred at room temperature for 3 h. The THF was evaporated, the pH adjusted to 4 and the solution extracted with EtOAc, dried over MgSO$_4$, filtered and evaporated to afford the title compound as an off-white solid (0.137 g, 81%). δH (CD$_3$OD), 8.55 (2H, s), 8.15–7.35 (6H, m), 7.25 (2H, d, J 7.02 Hz), 4.97 (1H, m) and 3.25–3.13 (2H, m). m/z (ES) 483 (MH$^+$).

EXAMPLE 7

[N-3-(1-H-Tetrazol-5-yl)benzoyl]-(N'-3,5-dichloroisonicotinoyl)-L-4-aminophenylalanine To Intermediate 10 (0.214 g, 0.396 mmol) in MeOH (5 ml) and water (5 ml) was added lithium hydroxide monohydrate (25 mg) and the reaction stirred at room temperature for 3 h. The meOH was evaporated and the pH was adjusted to 6.5 using 1M hydrochloric acid. A white solid appeared, which was filtered and washed with EtOAc. The solid was then passed through a Dowex-50WX4-400 ion exchange column eluting with CH$_3$CN/water (50:50) to afford the title compound as a white solid (0.088 g, 42%). δH (CD$_3$OD) 8.60 (2H, s), 8.40 (1H, s), 8.15 (1H, d, J 7.8 Hz), 7.9 (1H, d, J 7.8 Hz), 7.68–7.51 (3H, m), 7.3 (2H, d, J 8.5 Hz), 4.95–4.85 (1H, m) and 3.39–3.08 (2H, m). m/z (ES) 526 (MH$^+$).

EXAMPLE 8

[N-(3-Methoxycarbonylbenzoyl)]-(N'-3,5-dichloroisonicotinoyl)-L-4-aminophenylalnine To Intermediate 4c) (0.39 g) in dry DCM (5 ml) was added trifluoroacetic acid (1 ml) and the reaction stirred for 3 h. Further trifluoroacetic acid (1.5 ml) and DCM (5 ml) were added and the reaction stirred for a total of 6 h. The mixture was evaporated, acetonitrile/water was added and freeze drying afforded the title compound as a white solid (0.257 g, 60%). δH (CD$_3$OD), 8.61 (2H, s), 7.85–7.03 (8H,m), 4.89 (1H, m), 3.69 (3H, s) and 3.1–3.0 (2H, m). m/z (ES) 516 (MH$^+$).

The following assays can be used to demonstrate the potency and selectivity of the compounds according to the invention. In each of these assays an IC$_{50}$ value was determined for each test compound and represents the concentration of compound necessary to achieve 50% inhibition of cell adhesion where 100%=adhesion assessed in the absence of the test compound and 0%=absorbance in wells that did not receive cells.

$\alpha_4\beta_1$ Integrin-dependent Jurkat Cell Adhesion to VCAM-Ig 96 well NUNC plates were coated with F(ab)$_2$ fragment goat anti-human IgG Fcγ-specific antibody [Jackson Immuno Research 109-006-098: 100 μl at 2 μg/ml in 0.1M NaHCO$_3$, pH 8.4], overnight at 4°. The plates were washed (3×) in phosphate-buffered saline (PBS) and then blocked for 1 h in PBS/1% BSA at room temperature on a rocking platform. After washing (3×in PBS) 9 ng/ml of purified 2d VCAM-lg diluted in PBS/1% BSA was added and the plates left for 60 minutes at room temperature on a rocking platform. The plates were washed (3× in PBS) and the assay then performed at 37° for 30 min. in a total volume of 200 μl containing 2.5×10$^5$ Jurkat cells in the presence or absence of titrated test compounds.

Each plate was washed (2×) with medium and the adherent cells were fixed with 100 μl methanol for 10 minutes followed by another wash. 100 μl 0.25% Rose Bengal (Sigma R$_{4507}$) in PBS was added for 5 minutes at room temperature and the plates washed (3×) in PBS. 100 μl 50% (v/v) ethanol in PBS was added and the plates left for 60 min after which the absorbance (570 nm) was measured.

$\alpha_4\beta_7$ Integrin-dependent JY Cell Adhesion to MAdCAM-Ig

This assay was performed in the same manner as the $\alpha_4\beta_1$ assay except that MAdCAM-Ig (150 ng/ml) was used in place of 2d VCAM-Ig and a sub-line of the β-lympho blastoid cell-line JY was used in place of Jurkat cells. The IC$_{50}$ value for each test compound was determined as described in the $\alpha_4\beta_1$ integrin assay.

$\alpha_5\beta_1$ Integrin-dependent K562 Cell Adhesion to Fibronectin 96 well tissue culture plates were coated with human plasma fibronectin (Sigma F0895) at 5 ug/ml in phosphate-buffered saline (PBS) for 2 hr at 37° C. The plates were washed (3×in PBS) and then blocked for 1 h in 100 μl PBS/1% BSA at room temperature on a rocking platform. The blocked plates were washed (3×in PBS) and the assay then performed at 37° C. in a total volume of 200μl containing 2.5×10$^5$ K562 cells, phorbol-12-myristate-13-acetate at 10 ng/ml, and in the presence or absence of titrated test compounds. Incubation time was 30 minutes. Each plate was fixed and stained as described in the $\alpha_4\beta_1$ assay above.

$\alpha_m\beta_2$-Dependent Human Polymorphonuclear Neutrophils Adhesion to Plastic 96 well tissue culture plates were coated with RPMI 1640/10% FCS for 2 h at 37° C. 2×10$^5$ freshly isolated human venous polymorphonuclear neutrophils (PMN) were added to the wells in a total volume of 200 μl in the presence of 10 ng/ml phorbol-12-myristate-13-acetate, and in the presence or absence of test compounds, and incubated for 20 min at 37° C. followed by 30 min at room temperature. The plates were washed in medium and 100 μl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% H$_2$O$_2$ (Sigma) and 50μg/ml TMB (Boehringer Mannheim) in 0.1M sodium acetate/citrate buffer, pH 6.0 and absorbance measured at 630 nm.

αIIb/β$_3$-Dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of 6×10$^8$/ml in autologous plasma. Cuvettes contained equal volumes of PRP and filtered Tyrode's buffer (g/liter: NaCl 8.0; MgCl$_2$.H$_2$O 0.427; CaCl$_2$ 0.2; KCl 0.2: D-glucose 1.0; NaHCO$_3$ 1.0; NaHPO$_4$.2H$_2$O 0.065). Aggregation was monitored following addition of 2.5 μM ADP (Sigma) in the presence or absence of inhibitors.

In the above assays the compounds of the invention generally have IC$_{50}$ values in the $\alpha_4\beta_1$ and $\alpha_4\beta_7$ assays of 1 μM and below. Compounds of the Examples typically had IC$_{50}$ values of 100 nM and below in these assays and demonstrated selective inhibition of α$_4$β$_1$. In the other assays featuring α integrins of other subgroups the same compounds had IC$_{50}$ values of 50 μM and above thus demonstrating the potency and selectivity of their action against α$_4$ integrins.

What is claimed is:

1. A compound of formula (1b):

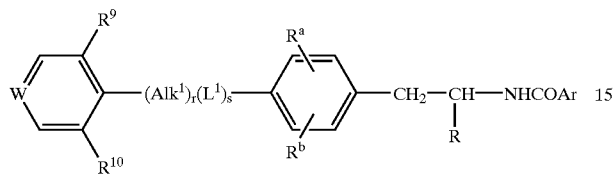

(1b)

wherein:
R is a carboxylic acid or a derivative thereof;
W is —N═;
—(Alk$^1$)$_r$(L$^1$)$_s$— is a —CON(R$^4$)— group;
R$^4$ is a hydrogen atom or a straight or branched alkyl group;
R$^a$, R$^b$, R$^9$ and R$^{10}$, which are the same or different, is each an atom or group —L$^2$(CH$_2$)$_p$L$^3$(R$^c$))$_q$;
L$^2$ and L$^3$ is each a covalent bond or a linker atom or group;
R$^c$ is a hydrogen or halogen atom or a group selected from a straight or branched alkyl, OR$^d$, SR$^d$, NR$^d$R$^e$, —NO$_2$, —CN, —CO$_2$R$^d$, —N(R$^d$)COR$^e$, —NR(R$^d$)CSR$^e$, —SO$_2$NR$^d$R$^e$, —N(R$^d$)SO$_2$R$^e$, —N(R$^d$)CONR$^d$R$^f$, —N(R)CSNR$^d$R$^f$ or —N(R$^d$)SO$_2$NR$^d$R$^f$ group;
R$^d$, R$^e$ and R$^f$, which are the same or different, is each a hydrogen atom or an optionally substituted straight or branched alkyl group;
p is zero or the integer 1;
q is an integer 1, 2 or 3;
Ar is an optionally substituted aromatic group;
and the salts, solvates, hydrates and N-oxides thereof.

2. A compound according to claim 1 wherein R$^4$ is a hydrogen atom.

3. A compound according to claim 1 wherein R$^9$ and R$^{10}$, which are the same or different, is each a hydrogen, fluorine or chlorine atom or a group selected from a methyl, ethyl, methoxy, ethoxy, —CF$_3$, —OH, —CN, —NO$_2$, NHCH$_3$, —N(CH$_3$)$_2$, —COCH$_3$, —SCH$_3$, —CO$_2$H, or —CO$_2$CH$_3$ group.

4. A compound which is selected from the group consisting of:

2-Carboxybenzoyl-(N'-3,5-dichloroisonicotinoyl)-L-4aminophenylalanine;

(N-2,6-Dimethoxybenzoyl)-(N'-3,5-dichloroisonicotinoyl)-L-4-aminophenylalanine;

(N-3-Carboxybenzoyl)-(N'-3,5-dichloroisonicotinoyl)-L-4-aminophenylalanine;

(N-4-Carboxybenzoyl)-(N'-3,5-dichloroisonicotinoyl)-L-4-aminophenylalanine;

(N-2-t-Butoxycarbonylbenzoyl)-(N'-3,5-dichloroisonicotinoyl)-L-4-aminophenylalanine;

(N-3-Cyanobazyl)-(N'-3,5-dichloraisoicotinoyl)-L-4-amiophenylalanine;

[N-3-(1-H-Tetrazol-5-yl)benzoyl]-(N'-3,5-dichloroisonicotinoyl)-L-4-aminophenylalanine;

[N-(3-Methoxycarbonylbenzoyl)]-(N'-3,5-dichloroisonicotinoyl)-L-4-aminophenylalanine;

and the salts, solvates, hydrates and N-oxides thereof.

5. A compound according to claim 1 wherein Ar is an optionally substituted phenyl group.

6. A compound according to claim 1 wherein R is a —CO$_2$H group.

7. A pharmaceutical composition comprising an effective amount a compound according to claim 1 together with one or more pharmaceutically acceptable carriers, excipients or diluents.

8. A compound according to claim 4 which is (N-2,6-Dimethoxybenzoyl)-(N'-3,5-dichloroisonicotinoyl)-L-4-aminophenylalanine; and the salts, solvates, hydrates and N-oxides thereof.

9. A compound according to claim 1, wherein Ar is an optionally substituted phenyl group.

* * * * *